(12) United States Patent
Yoshida et al.

(10) Patent No.: US 7,858,799 B2
(45) Date of Patent: Dec. 28, 2010

(54) IONIC ORGANIC COMPOUND

(75) Inventors: Masaru Yoshida, Tsukuba (JP);
Nagatoshi Koumura, Tsukuba (JP);
Nobuyuki Tamaoki, Tsukuba (JP);
Hajime Kawanami, Sendai (JP);
Hajime Matsumoto, Ikeda (JP); Said Kazaoui, Tsukuba (JP); Nobutsugu Minami, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 484 days.

(21) Appl. No.: 11/883,462

(22) PCT Filed: Jan. 30, 2006

(86) PCT No.: PCT/JP2006/301402
§ 371 (c)(1),
(2), (4) Date: Sep. 28, 2007

(87) PCT Pub. No.: WO2006/082768
PCT Pub. Date: Aug. 10, 2006

(65) Prior Publication Data
US 2008/0210907 A1    Sep. 4, 2008

(30) Foreign Application Priority Data

| Feb. 2, 2005 | (JP) | ............................... 2005-025754 |
| Feb. 17, 2005 | (JP) | ............................... 2005-040532 |
| Feb. 28, 2005 | (JP) | ............................... 2005-053920 |
| Jul. 22, 2005 | (JP) | ............................... 2005-212138 |
| Sep. 20, 2005 | (JP) | ............................... 2005-272750 |
| Oct. 24, 2005 | (JP) | ............................... 2005-308037 |

(51) Int. Cl.
*C07D 211/84* (2006.01)
*C07D 401/04* (2006.01)
*C09K 11/65* (2006.01)

(52) U.S. Cl. ........................ 546/255; 544/169; 544/211; 544/353; 546/143; 546/194; 546/309; 548/195; 548/265.4; 548/338.1; 106/287.2; 252/301.26; 252/301.36

(58) Field of Classification Search ........................ None
See application file for complete search history.

(56) References Cited

U.S. PATENT DOCUMENTS

| 6,268,092 B1 | 7/2001 | Akashi et al. |
| 6,682,677 B2 | 1/2004 | Lobovsky et al. |
| 2002/0029574 A1 | 3/2002 | Yoshioka |
| 2002/0065329 A1 | 5/2002 | Kimizuka et al. |

2005/0156144 A1    7/2005  Fukushima et al.

FOREIGN PATENT DOCUMENTS

| JP | 5-501731 A | 4/1993 |
| JP | 2001-33832 A | 2/2001 |
| JP | 2002-3478 A | 1/2002 |
| JP | 2002-85957 A | 3/2002 |
| JP | 2002-85958 A | 3/2002 |
| JP | 2003-049154 A | 2/2003 |
| JP | 2003-055642 A | 2/2003 |
| JP | 2003-233148 A | 8/2003 |
| JP | 2003-238126 A | 8/2003 |
| JP | 2003-257240 A | 9/2003 |
| JP | 2003-327949 A | 11/2003 |
| JP | 2004-142972 A | 5/2004 |
| JP | 2004-532937 A | 10/2004 |
| WO | WO 91/08248 A1 | 6/1991 |

OTHER PUBLICATIONS

Baker et al, Journal of Medicinal Chemistry (1969), 12(2), 221-4.*
Nowak et al., Nature, May 23, 2002, vol. 417, pp. 424-428.
Kubo et al., Chem. Commun., 2002, pp. 374-375.
O'Connell et al., Science, Jul. 26, 2002, vol. 297, pp. 593-596.
Fukushima et al., Science, Jun. 27, 2003, vol. 300, pp. 2072-2074.
Office Action in Japanese Application No. 2007-501550 mailed Aug. 31, 2010, including a partial English translation.

* cited by examiner

*Primary Examiner*—Zinna N Davis
(74) *Attorney, Agent, or Firm*—Birch, Stewart, Kolasch & Birch, LLP

(57) ABSTRACT

An ionic organic compound having a repeating unit of formula (I) can be synthesized easily from a readily available organic compound through a small number of reaction steps, can be produced without any purification technique such as chromatography, and can be used in a quite small amount for gelation of water or an ionic liquid without any other auxiliary solvent:

$$[-(A-B-C)_n-]\cdot m(X) \qquad (I)$$

wherein A represents a group having a quaternary ammonium cation which is formed from a heterocyclic compound having at least one nitrogen atom; B represents a functional group, which may have a substituent, selected from amide, urea, urethane and peptide groups; C represents a divalent hydrocarbon group, which may have a substituent, capable of linking between A and B; X represents an anion; n represents the number of repeating units; m represents the total number of anions; and n and m are the same integer. A hydrogel using the compound is stable under acidic conditions, capable of setting a large amount of water with a small amount thereof, and capable of quickly recovering the original elastic modulus against structural disruption caused by mechanical distortion. The hydrogel is capable of directly gelling an ionic liquid without other solvent such as water when causing gelation. Further, the hydrogel is capable of easily dispersing carbon nanotubes in water whose load on the environment is low.

19 Claims, 10 Drawing Sheets a)

b)

(a) (b)

IONIC ORGANIC COMPOUND

TECHNICAL FIELD

The present invention relates to a novel ionic organic compound useful as a gelling agent, a solid-dispersing agent, or the like. More specifically, the present invention relates to: a novel ionic organic compound useful as a gelling agent capable of gelling a medium such as water and an ionic liquid, useful for a hydrogel or an ionic liquid gel containing such a gelling agent, and useful as a dispersing agent for dispersing single-walled carbon nanotubes into water; a method for producing the compound; and a gelling agent, a gel and a dispersing agent each using the compound.

BACKGROUND ART

In recent years, "gels" as soft materials are expected to be applied for industrial purposes in a wide range of fields such as food products, cosmetics, sport shoes, and chromatography.

Many of them, however, are natural gels, such as agar, gelatin, and carrageenan, and their function has limits. It is also difficult to further impart an optimal function only by chemical modification thereof.

Under the circumstances, recently, basic research and application development have been actively conducted on synthetic gels artificially mimicking the functions of natural gels.

A known example of such synthetic gelling agents is a hydrogel-forming agent using a polymer such as polyacrylic acid. However, hydrogels produced with such a polymer gelling agent are irreversible chemical gels that cannot return to the original water once formed, and it is impossible to control the physical properties of the formed gels, such as the hardness and thermal stability of the gels.

Furthermore, recently, there are also proposed some synthetic hydrogel-forming agents using biodegradable or biocompatible molecular structure units (for example, see Patent Documents 1 to 3 below). Each of these agents requires a multi-step process of synthetic steps and separation operation, and thus presents a significant challenge to large-scale synthesis for practical use.

Furthermore, conventional synthetic hydrogel-forming agents and natural hydrogel-forming agents (agar) also have a problem in which adaptable aqueous solutions are limited to those with acidity close to neutral, because they contain, in their molecular structure, an acetal bond or ester bond which is unstable under acidic conditions.

In addition, hydrogels produced with these gelling agents show slow equilibrium between a quasi-solid state under no-mechanical load conditions and a quasi-liquid state produced under high distortion conditions. Once the quasi-solid structure of such hydrogels is collapsed by mechanical impact, it generally takes a long period of time, for example, the order of several hours to several days for gelatin, to recover the structure. This significantly limits the applicability of the gels.

In order to solve this problem, there is proposed a copolymer macromolecular gelling agent having a charge in its side chain (for example, see Non-Patent Document 1 below). However, it is complex in structure and synthesis and thus cannot be popular.

There is also a demand for artificial gelling agents adaptable to not only water but also a wide variety of solvents. For example, since ionic liquids are non-volatile and highly ion-conductive, gels thereof made by gelling those are expected to find applications in the field of cells, such as solid (quasi-solid) electrolytes for secondary cells and sensors, and expected to be applied to organic synthesis reactions in gelled liquids.

Several types of low-molecular compounds capable of gelling such ionic liquids have been synthesized and developed in the past (for example, see Patent Document 4 and Non-Patent Document 2 below). Each of these compounds has a complicated molecular structure and thus requires a multi-step synthetic process and separation/purification operation. They are also known to reduce their ion conductivity (electrical conductivity) due to an increase in viscosity after the gelation, which is a challenge to be overcome as soon as possible.

There is also proposed another synthetic polymer gelling agent (for example, see Patent Document 5 below). However, a relatively large amount of such a gelling agent is necessary for gelation of ionic liquids, and there is a problem in which since an additional solvent such as water and acetone is often used for the gelation, the process of forming a gel consisting of a pure ionic liquid has to undergo high temperature drying for removing such an auxiliary solvent.

Furthermore, concerning polymer gelling agents, a method is developed which uses a thermally irreversible chemical gel (see Non-Patent Documents 3 and 4 below). This method includes mixing an ionic liquid electrolyte, a gelling agent, and a crosslinking agent, to form a gel electrolyte precursor, injecting the precursor into a cell, and then heating the precursor, to cause gelation in the cell. However, the gel has a chemically-bonded, three-dimensional, network structure and thus does not return to a solution state even at high temperature.

On the other hand, carbon nanotubes are attracting attention as useful materials for nanotechnology and expected to be applied in a wide range of fields such as transistors, electron emission electrodes, fuel cell electrodes, and scanning microscope chips. When they are purified or prepared for applications as materials for the applications, it is necessary to prepare an easily handleable carbon nanotube solution or dispersion (dispersed liquid) or a gel containing it.

Thus, there is proposed a method for making hydrophobic carbon nanotubes soluble in a solvent, which includes adding a dispersing agent (generally an amphiphilic surfactant) to form a dispersion liquid (for example, see Patent Document 6 and Non-Patent Document 3). Under the present circumstances, however, investigations for further improvements are still being carried out.

Hitherto, Patent Document 7 and Non-Patent Document 4 listed below are known to disclose carbon nanotube-containing gel materials. In this technique, however, it is necessary to use a special solvent of an ionic liquid, and thus it is difficult to prepare a gel with a low environmental-load common solvent such as water.

As described above, conventional gelling agents only have a gelling function. At present, there has been developed no artificial gelling agent having another function such as a dispersing function in combination with a gelling function, and for example being capable of dispersing single-walled carbon nanotubes in a medium of water and forming a gel at the same time.

Patent Document 1: JP-A-2003-327949
Patent Document 2: JP-A-2003-49154
Patent Document 3: JP-A-2003-55642
Patent Document 4: JP-A-2002-3478
Patent Document 5: JP-2003-257240
Patent Document 6: JP-A-2003-238126
Patent Document 7: JP-A-2004-142972

Non-Patent Document 1: Nature, Vol. 417, p. 424 (2002).
Non-Patent Document 2: Chem. Commun. 2002, p. 374.
Non-Patent Document 3: Science, Vol. 297, p. 593 (2002).
Non-Patent Document 4: Science, Vol. 300, p. 2072 (2003).

DISCLOSURE OF INVENTION

Problems that the Invention is to Solve

The present invention has been made in order to overcome the above problems with conventional technology. A first object of the present invention is to provide a novel ionic organic compound that can be synthesized from readily available organic compounds by a simple process of a small number of reaction steps, can be obtained without using such a purification technique as chromatography, and can gel water or an ionic liquid with a very small amount thereof without other auxiliary solvents; and to provide a simple method for production thereof.

A second object of the present invention is to provide a hydrogel-forming agent stable under acidic conditions and capable of gelling a large amount of water with a small amount thereof; and to provide a hydrogel capable of quickly recovering the original elastic modulus against structural destruction by mechanical distortion. A third object of the present invention is to provide a good ionic liquid-gelling agent capable of directly gelling an ionic liquid without other solvents such as water when causing gelation; and to provide an ionic liquid gel that does not lose ionic conductivity after gelation and is useful as a solid electrolyte or the like.

A fourth object of the present invention is to provide a carbon nanotube-dispersing agent capable of easily dispersing carbon nanotubes in water, whose load on the environment is low, and to provide a dispersion liquid therewith, a dispersion gel, a thin film, and a light-emitting material each using the dispersing agent.

Means to Solve the Problem

The inventors of the present invention have focused attention on self-organization phenomena spotlighted in the nanotechnology field, and developed a variety of organic gelling agents capable of inducing gelation generally in organic solvents.

Based on the research background, the inventors have found ionic organic compounds, which are available by a simple synthetic reaction and capable of gelling water or an ionic liquid with a very small amount thereof without other auxiliary solvents, which can give a hydrogel capable of quickly recovering the original elastic modulus against structural destruction by mechanical distortion or give an ionic liquid gel that does not lose ionic conductivity after gelation and that is useful as a solid electrolyte or the like, and which can be used as a carbon nanotube-dispersing agent or a carbon nanotube-gelling agent. Based on the finding, the present invention has been completed.

That is, according to this application, the following inventions are to be provided:

[1] An ionic organic compound, having a repeating unit represented by formula (I):

[Formula 1]

$$[-(A-B-C)_n-]\bullet m(X) \qquad (I)$$

wherein A represents a quaternary ammonium cation-containing group derived from a heterocyclic compound containing at least one nitrogen atom; B represents a functional group selected from an amide group, a urea group, a urethane group, and a peptide group, each of which may have a substituent(s); C represents a divalent hydrocarbon group linking A and B, which group may have a substituent; X represents an anion; n represents the number of repeating units; m represents the total number of anions; and n and m are the same integer.

[2] The ionic organic compound according to [1], wherein with respect to A of formula (I), the heterocyclic compound containing at least one nitrogen atom is an aromatic heterocyclic compound.

[3] The ionic organic compound according to [2], wherein the aromatic heterocyclic compound is at least one selected from pyridine, pyrazine, pyrimidine, triazine, quinoline, isoquinoline, quinoxaline, imidazole, thiazole, and triazole, each of which may have a substituent(s).

[4] The ionic organic compound according to any one of [1] to [3], wherein, in formula (I), B is at least one selected from an amide group, a urea group, a urethane group, and a peptide group.

[5] The ionic organic compound according to any one of [1] to [4], wherein the divalent hydrocarbon group of C in formula (I) is an optionally substituted aliphatic hydrocarbon group or an optionally substituted aromatic hydrocarbon group.

[6] The ionic organic compound according to any one of [1] to [5], wherein n and m in formula (I) are each an integer of 2 to 30.

[7] The ionic organic compound according to any one of [1] to [6], wherein X in formula (I) is at least one selected from a halogen atom (F, Cl, Br, or I), a tetrafluoroborate group ($BF_4$), a hexafluorophosphate group ($PF_6$), bis(trifluoromethanesulfonyl)imide, thiocyanate (SCN), a nitrate group ($NO_3$), a sulfate group ($SO_4$), a thiosulfate group ($S_2O_3$), a carbonate group ($CO_3$), a hydrogencarbonate group ($HCO_3$), a phosphate group, a phosphite group, a hypophosphite group, any halogen oxide acid group ($XO_4$, $XO_3$, $XO_2$, or XO, wherein X is Cl, Br or I), a tris(trifluoromethylsulfonyl)carbon acid group, a trifluoromethylsulfonate group, a dicyanamide group, an acetate group ($CH_3COO$), a haloacetate group (($CX_nH_{3-n}$)COO, wherein X is F, Cl, Br, or I, and n is 1, 2 or 3), and a tetraphenylborate group ($BPh_4$) and a derivative thereof ($B(Aryl)_4$, wherein Aryl is a substituted phenyl group).

[8] A method for producing the ionic organic compound according to any one of [1] to [7], comprising allowing an aminopyridine to undergo a condensation reaction with a halogenomethylcarboxylic acid halide having an active methylene group in its molecule or with an isocyanate compound having an active methylene group in its molecule.

[9] A method for producing the ionic organic compound according to any one of [1] to [7], comprising replacing the anion of the ionic organic compound produced by the method according to [8] with another anion by an anion exchange reaction.

[10] A hydrogel-forming agent, comprising the ionic organic compound according to any one of [1] to [7] as an essential component.

[11] A hydrogel, comprising the hydrogel-forming agent according to [10].

[12] The hydrogel according to [1,1], which has a high-speed storage modulus-recovery rate.

[13] The hydrogel according to [1,2], wherein when the hydrogel with a concentration of 30 g/L is measured for dynamic viscoelasticity at 25° C., the resulting physical property values are: a storage modulus (G') of 1,000 Pa to 50,000 Pa and a loss tangent (tand) of at most 0.5 indicating quasi-solid properties, at a frequency of 6 rad/s and a distortion of 0.02%; and a storage modulus (Gs') of 1 Pa to 100 Pa and a loss tangent (tand) of at least 2 indicating quasi-liquid properties, at a frequency of 6 rad/s and a distortion of 100%, and when a distortion of 100% is continuously applied to the hydrogel for at least 1 minute, and immediately after that the resulting hydrogel be in a quasi-liquid state, the distortion is adjusted to 0.02% again, the hydrogel shows a storage modulus recovery rate (G'/G0') of more than 75% within 10 seconds and shows a storage modulus recovery rate (G'/G0') of more than 90% within 10 minutes, relative to its initial storage modulus value (G0').

[13] An ionic liquid-gelling agent, comprising the ionic organic compound according to any one of [1] to [7] as an essential component.

[14] An ionic liquid gel, comprising the ionic liquid-gelling agent according to [13].

[15] The ionic liquid gel according to [1,4], which has at least 85% of an ionic conductivity before gelation.

[16] A carbon nanotube-dispersing agent, comprising the ionic organic compound according to any one of [1] to [7] as an essential component.

[17] A carbon nanotube-dispersed liquid or gel, comprising the carbon nanotube-dispersing agent according to [1,6], carbon nanotubes, and a solvent comprising at least water.

[18] A carbon nanotube-containing thin film produced from the carbon nanotube-dispersed liquid or carbon nanotube-dispersed gel according to [17].

[19] The carbon nanotube-containing thin film according to [1,8], which is produced by spreading the carbon nanotube-dispersed liquid or carbon nanotube-dispersed gel on a substrate, followed by drying.

[20] The carbon nanotube-containing thin film according to [1,8] or [1,9], wherein the carbon nanotubes are dispersed in such a manner that they are separated from one another.

[21] A light-emitting material, comprising the carbon nanotube-containing thin film according to any one of [18] to [20].

Effects of the Invention (1) The ionic organic compound of the present invention is favorable for industrial-scale production, because it can be synthesized by a simple process of a small number of reaction steps, such as a one-step process or a two-step process, from readily available organic compounds and because it does not require any special purification operation.

(2) The ionic organic compound of the present invention is useful as a hydrogel-forming agent for setting a large amount of water with a very small amount of it and may be used as a water-retaining agent (for greening deserts, retaining water in plant culture soil, or the like), as a water-absorbing agent (for urine absorption in pet litters, moisture absorption in sanitary products, or the like).

The gelling agent composed of the ionic compound has an electrolyte structure charged by itself and thus may be applied to an electrolyte gel serving as an electronic material. The gelling agent may also be used as a moisturizing agent or the like in a wide range of fields such as the fields of fine chemical industry, pharmaceuticals, cosmetics, and the like. The hydrogel can quickly recover its storage modulus against structural destruction by mechanical distortion comparing to known conventional hydrogels, and thus is promising as a shock absorber, a base material for soft actuators, and an agent for controlling paint material running.

(3) The ionic organic compound of the present invention can gel various types of ionic liquids with a very small amount and thus is useful as an ionic liquid-gelling agent.

The ionic organic compound of the present invention can easily and directly produce an ionic liquid gel at low concentrations without any auxiliary solvent, which would otherwise be conventionally used as a medium, and the thus-prepared ionic liquid gel has the advantage that it does not lose the ionic conductivity of the ionic liquid before the gelation.

The ionic liquid gel is also useful as a quasi-solid prevented from causing the problem of leakage or the like, in practical applications such as electrolytes for lithium ion batteries and the like, and can be used to form various sensors with electrodes immersed or dipped therein or used as a new solid electrolyte material.

(4) The ionic organic compound of the present invention allows uniform dispersion of carbon nanotubes in water, whose load on the environment is low, without the use of any high environmental-load solvent such as an organic solvent, and allows gelation thereof.

Using the resulting carbon nanotube-dispersed liquid, a dispersion with high electrical conductivity and good semi-conducting properties can be easily produced at room temperature. A carbon nanotube-dispersed gel (or carbon nanotube-containing hydrogel) can also be easily synthesized, and thus can be expected to be applied to or developed for intelligent materials for electric actuators and the like. Furthermore, from the dispersion liquid or gel described above, a carbon nanotube-containing thin film can be easily formed, the thickness of which can also be readily and uniformly controlled and provided. An electron emission device using carbon nanotubes as an electron emission source or a light-emitting material using carbon nanotubes as an emitter can also be obtained therewith.

BEST MODE FOR CARRYING OUT THE INVENTION

Figure 1:
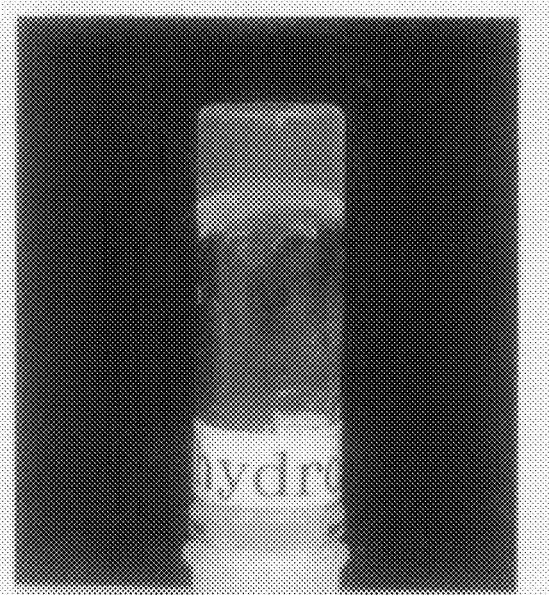
FIG. 1 is a photograph of a hydrogel in a sample tube, which is prepared using an ionic organic compound 1•Cl of the present invention as a gelling agent.

The novel ionic organic compound according to the present invention is represented by formula (I):

[Formula 1]

$$[-(A-B-C)_n-]\cdot m(X) \quad (I)$$

wherein A represents a quaternary ammonium cation-containing group derived from a heterocyclic compound containing at least one nitrogen atom; B represents a functional group selected from an amide group, a urea group, a urethane group, and a peptide group, each of which may have a substituent(s); C represents a divalent hydrocarbon group linking A and B, which group may have a substituent; X represents an anion, n represents the number of repeating units, m represents the total number of anions, and n and m are the same integer.

In formula (I), A is a moiety that has ionic properties to impart solubility in water and ionic liquid, that can produce a strong affinity for aromatic compounds and the like, as called attractive "cation-π interaction", and that induces electrostatic interaction necessary for high-speed elastic modulus recovery.

Specifically, A means a quaternary ammonium cation-containing group derived from a heterocyclic compound containing at least one nitrogen atom.

Examples of the heterocyclic compound containing at least one nitrogen atom include pyridine, quinoline, isoquinoline, quinoxaline, piperidine, pyrrolidine, morpholine, and thiazole, each of which may have a substituent(s); and examples of the heterocyclic compound containing two or more nitrogen atoms include pyrazine, pyrimidine, triazine, piperazine, imidazole, and triazole, each of which may have a substituent(s).

The nitrogen-containing heterocyclic compound that can be preferably used in the present invention, is a nitrogen-containing heterocyclic compound that exhibits a so-called aromaticity.

Examples of such an aromatic nitrogen-containing heterocyclic compound include pyridine, pyrazine, pyrimidine, triazine, quinoline, isoquinoline, quinoxaline, imidazole, thiazole, and triazole, each of which may have a substituent(s).

Examples of the substituent include alkyl, aryl, ketone, aldehyde, carboxyl, ether, amino, halogen, silyl, and phosphine groups.

Concerning the position bonded to B and C in the heterocyclic compound containing at least one nitrogen atom, all the positional isomers (including three types (1,2-, 1,3- and 1,4-positional isomers) for six-membered cyclic compounds and two types (1,2- and 1,3-positional isomers) for five-membered cyclic compounds) should be taken into account.

In formula (I), B is a moiety that lies in the main chain of the ionic organic compound and can accelerate a self-organizing phenomenon (aggregation) necessary for gelation by causing intermolecular interaction through hydrogen bonding, so that it can finally function to form a gel in which a solution is set.

Specifically, B means a functional group selected from amide, urea, urethane, and peptide groups, each of which may have a substituent(s).

In this case, examples of the substituent include alkyl, aryl, ketone, aldehyde, carboxyl, ether, amino, halogen, silyl, and phosphine groups.

An amide, urea or urethane group is preferably used as B.

In formula (I), C is a moiety that bonds and polymerizes A and B, to amplify and combine their properties, so that it can finally function to form a gel.

Specifically, C is a divalent hydrocarbon group, which may have a substituent(s). Examples of the divalent hydrocarbon group include aliphatic hydrocarbon groups, such as linear alkylene groups represented by $C_nH_{2n}$ (wherein n is 1 to 18), cyclic alkylene groups represented by $C_nH_{2(n-1)}$ (wherein n is 3 to 8), and linear or cyclic alkylene groups having one or more unsaturated bond(s); and aromatic hydrocarbon groups, such as benzylene, phenethylene, pyridylmethylene, thienylmethylene, pyrrolylmethylene, phenylene, pyridylene, and thienylene groups.

In this case, examples of the substituent include alkyl, aryl, ketone, aldehyde, carboxyl, ether, amino, halogen, silyl, and phosphine groups.

A benzylene or alkylene group is preferably used as C.

In the formula (I), X represents an anion, n represents the number of repeating units, m represents the total number of anions, and n and m are the same integer.

Examples of X include at least one selected from a halogen atom (such as F, Cl, Br, and I), a tetrafluoroborate group ($BF_4$), a hexafluorophosphate group ($PF_6$), bis(trifluoromethanesulfonyl)imide, thiocyanate (SCN), a nitrate group ($NO_3$), a sulfate group ($SO_4$), a thiosulfate group ($S_2O_3$), a carbonate group ($CO_3$), a hydrogencarbonate group ($HCO_3$), a phosphate group, a phosphite group, a hypophosphite group, any halogen oxide acid group (such as $XO_4$, $XO_3$, $XO_2$, and XO, wherein X is Cl, Br or I), a tris(trifluoromethylsulfonyl)carbon acid group, a trifluoromethylsulfonate group, a dicyanamide group, an acetate group ($CH_3COO$), a haloacetate group (($CX_nH_{3-n}$)COO, wherein X is F, Cl, Br, or I, and n is 1, 2 or 3), and a tetraphenylborate group ($BPh_4$) and a derivative thereof ($B(Aryl)_4$, wherein Aryl is a substituted phenyl group).

Further, n and m each are an integer of 2 to 30, preferably 2 to 15.

Typical examples of the ionic organic compound represented by formula (I) according to the present invention include Compounds (A1) to (A25) shown below.

In each table/formula, X is at least one selected from a halogen atom (such as F, Cl, Br, and I), a tetrafluoroborate group ($BF_4$), a hexafluorophosphate group ($PF_6$), bis(trifluoromethanesulfonyl)imide, thiocyanate (SCN), a nitrate group ($NO_3$), a sulfate group ($SO_4$), a thiosulfate group ($S_2O_3$), a carbonate group ($CO_3$), a hydrogencarbonate group ($HCO_3$), a phosphate group, a phosphite group, a hypophosphite group, any halogen oxide acid group (such as $XO_4$, $XO_3$, $XO_2$, and XO, wherein X is Cl, Br or I), a tris(trifluoromethylsulfonyl)carbon acid group, a trifluoromethylsulfonate group, a dicyanamide group, an acetate group ($CH_3COO$), a haloacetate group (($CX_nH_{3-n}$)COO, wherein X is F, Cl, Br, or I, and n is 1, 2 or 3), and a tetraphenylborate group ($BPh_4$) and a derivative thereof ($B(Aryl)_4$, wherein Aryl is a substituted phenyl group).

TABLE 1

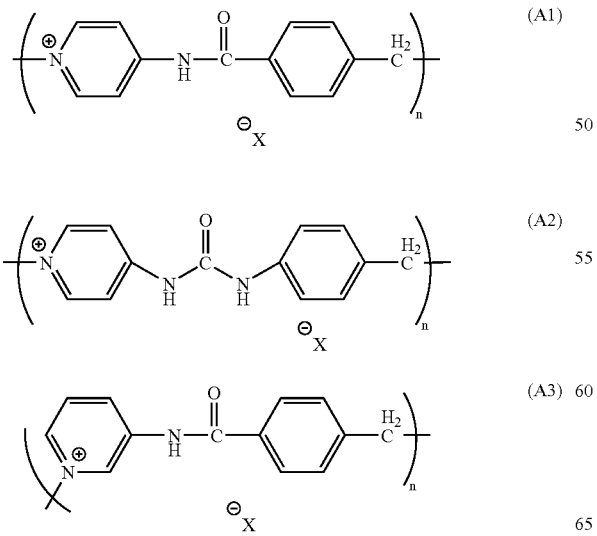

TABLE 1-continued

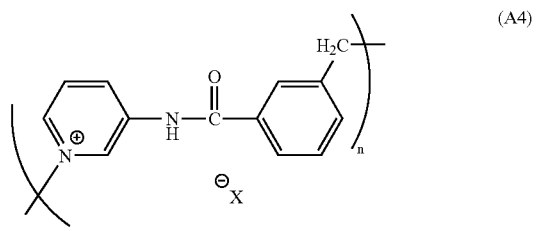
(A4)

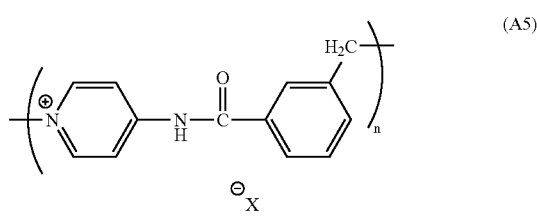
(A5)

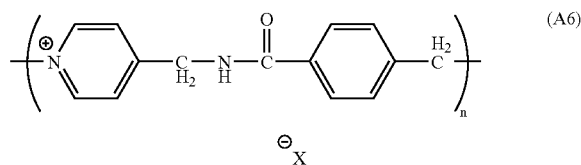
(A6)

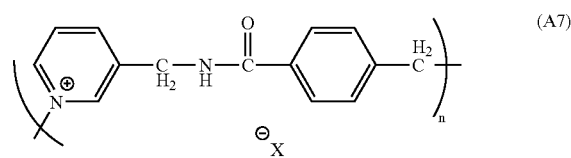
(A7)

TABLE 2

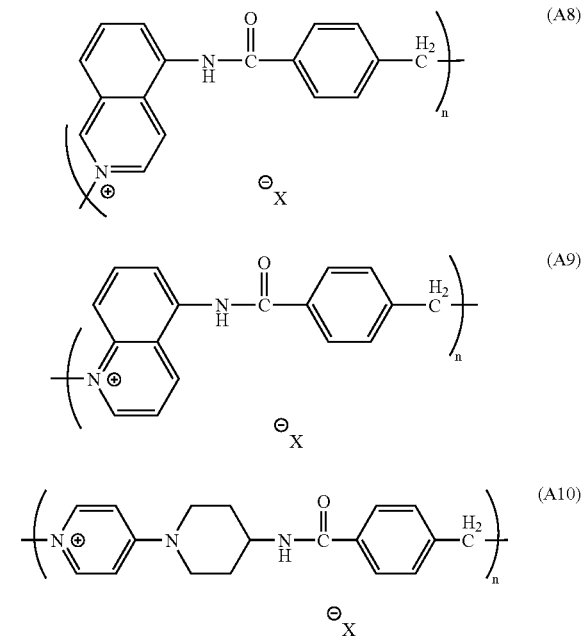

TABLE 2-continued
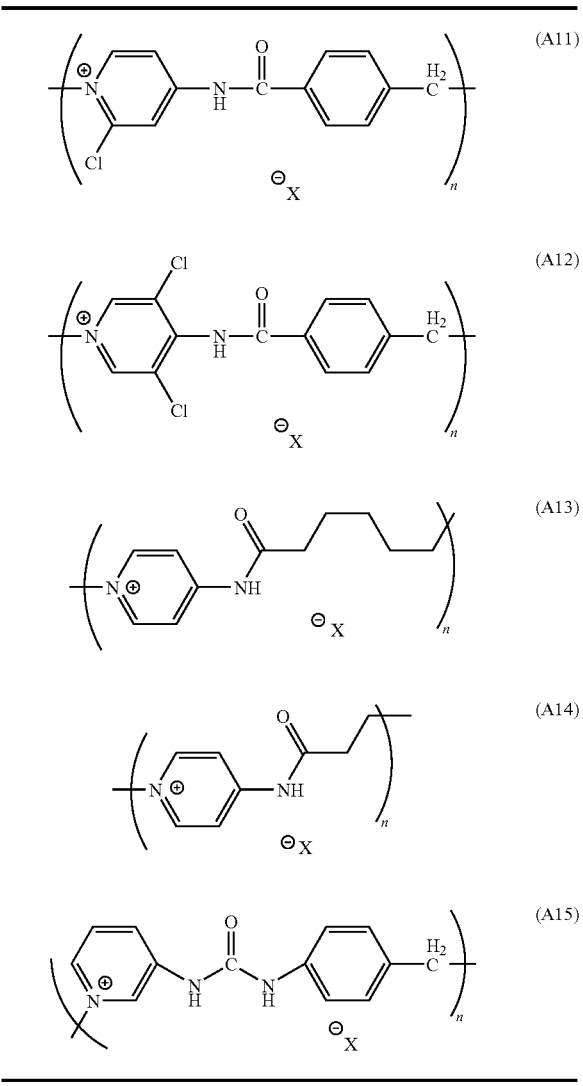
TABLE 3
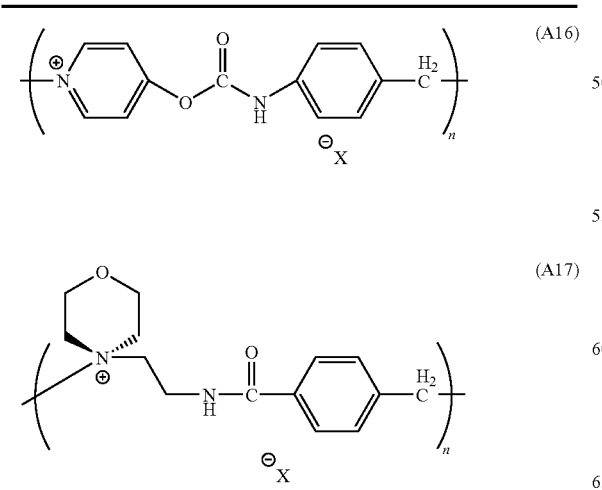
TABLE 3-continued
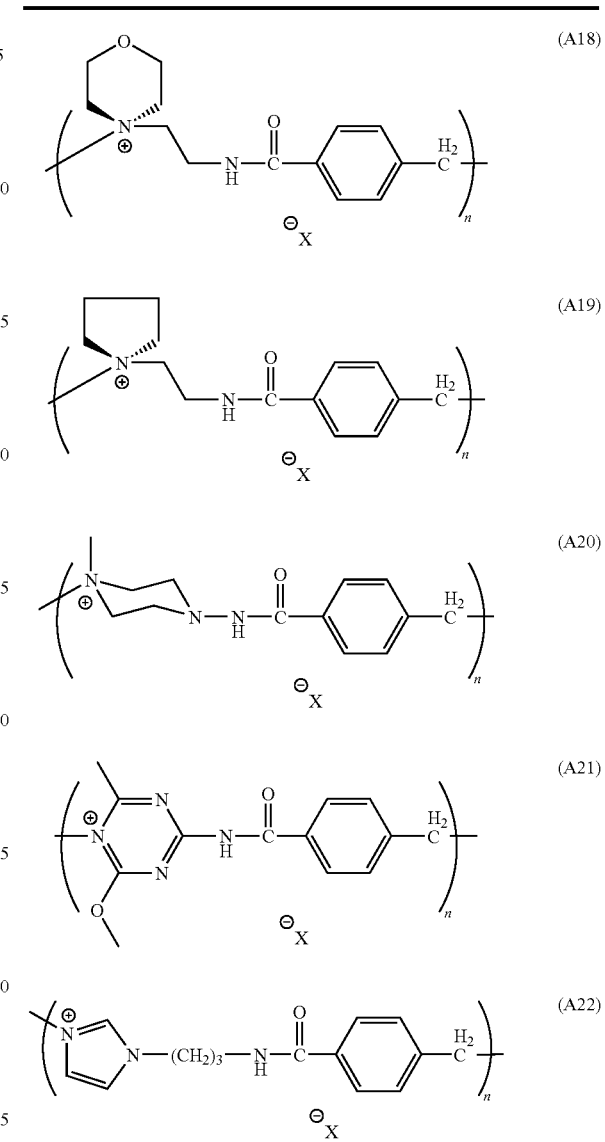
TABLE 4
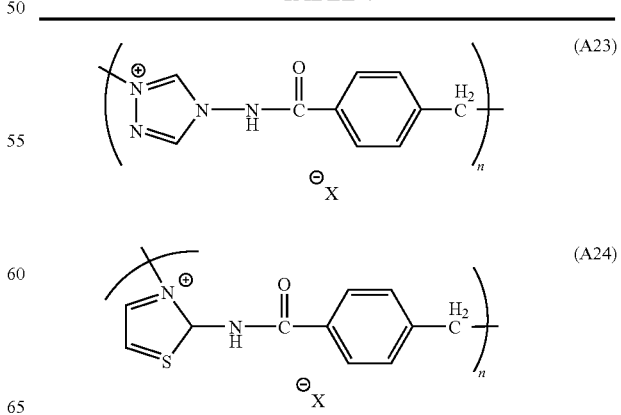

TABLE 4-continued

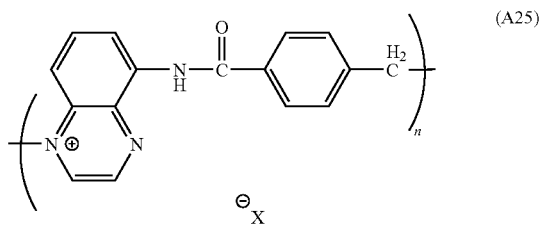

(A25)

The ionic organic compound represented by formula (I) may be synthesized by a simple process, such as (a) direct synthesis using an "ionic self-condensation" reaction or (b) a counter anion exchange reaction using, as a raw material, an ionic organic compound directly synthesized by the "ionic self-condensation" reaction.

When the ionic organic compound represented by formula (I) is produced by (a) the direct synthesis method, a heterocyclic compound containing at least one nitrogen atom having amino may be allowed to undergo a condensation reaction with a halogenomethylcarboxylic acid halide having an active methylene group in its molecule or with an isocyanate compound having an active methylene group in its molecule.

For example, an amidation reaction may be performed using an aminopyridine and benzoic acid chloride having an active methylene group in its molecule. In this process, a reactive amide compound is produced as an intermediate in the system, and then quaternarization and coupling reaction between the pyridine ring and the active methylene further cause spontaneous condensation, to give an ionic organic compound represented by formula (A1) in Table 1 and having an electrolyte structure.

This synthetic reaction can be represented by the following reaction scheme:

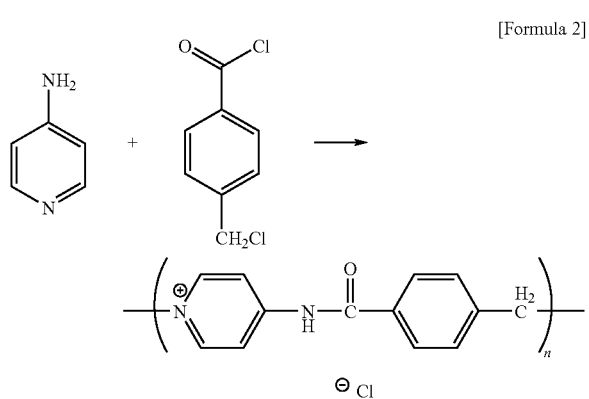

[Formula 2]

The above reaction is preferably performed in the presence of triethylamine in solution in a solvent with stirring. The solvent to be used may be an organic solvent. Ethers, hydrocarbons, chlorine atom-containing hydrocarbons, or the like may be used as the organic solvent. In particular, chlorine atom-containing hydrocarbons, specifically methylene chloride, are preferred in order to prevent the decomposition of chloromethylbenzoic acid chloride and to control the reaction. The reaction temperature is preferably in the range of 0 to 100° C., more preferably of 20 to 40° C. The reaction time is preferably from 12 to 50 hours, depending on the reaction temperature.

In this condensation polymerization reaction, a reactive amide compound is produced as an intermediate in the system, and then quaternarization and coupling reaction between the pyridine ring and the active methylene further cause spontaneous condensation, so that a polymerized ionic compound represented by formula (A1) above can be precipitated. The precipitated powder may be separated by filtration and washed with an organic solvent such as methylene chloride, so that the desired ionic compound can be easily obtained. At that time, any other purification operation does not have to be preformed.

When the ionic organic compound represented by formula (I), specifically the compound represented by formula (A2) in Table 1, is produced by (a) the direct synthesis method, for example, a pyridine compound having an amino group ($NH_2$) at the 4-position may be allowed to undergo a condensation reaction with a chloromethylbenzoic acid isocyanate compound having an active methylene group in its molecule. In this process, quaternarization and coupling reaction between the pyridine ring and the active methylene of the molecules further cause spontaneous condensation, so that the compound represented by formula (A2) in Table 1 and having an electrolyte structure can be obtained as a precipitate.

This synthetic reaction may be represented by the following reaction scheme:

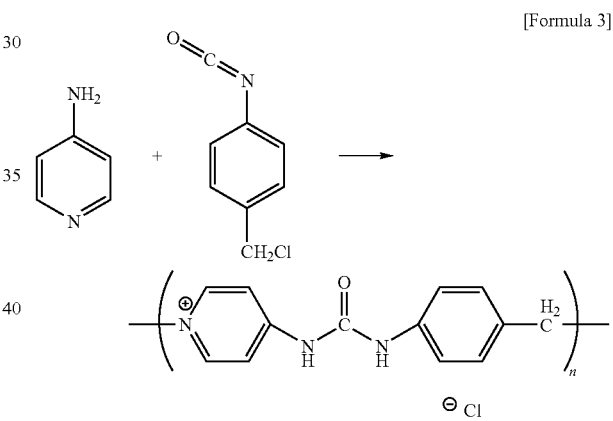

[Formula 3]

In the above reaction, the reactants of the pyridine derivative and the chloromethylbenzoic acid isocyanate compound may be used in a standard ratio of 1:1, and the reaction temperature may be at or near the boiling point of the solvent, and the reaction time may be in the range of about 1 to about 10 hours.

The above reaction can produce the corresponding compound in which n (the coefficient representing the number of units in the compound) is in the range of 2 to 30, generally in the range of 3 to 10. The coefficient n may be controlled by selecting the reaction conditions, specifically selecting the reaction temperature, the reaction time, the type of the reactants, and the ratio between the reactants to be used, and the like.

When the ionic organic compound represented by formula (I) is produced by (b) the counter anion exchange reaction, an ionic organic compound directly synthesized by the "ionic self-condensation" reaction may be used as a raw material, and an anion-containing compound different from the raw material compound may be allowed to react with the raw material, to undergo a counter anion exchange reaction.

For example, the ionic organic compound obtained by the direct synthesis method of formula (I) above may be dissolved in water and refluxed under heating at 100° C., and, for example, an aqueous solution of one atom or ion for X selected from a halogen atom (such as F, Cl, Br, and I), a tetrafluoroborate group ($BF_4$), a hexafluorophosphate group ($PF_6$), bis(trifluoromethanesulfonyl)imide, thiocyanate (SCN), a nitrate group ($NO_3$), a sulfate group ($SO_4$), a thiosulfate group ($S_2O_3$), a carbonate group ($CO_3$), a hydrogencarbonate group ($HCO_3$), a phosphate group, a phosphite group, a hypophosphite group, any halogen oxide acid group (such as $XO_4$, $XO_3$, $XO_2$, and $XO$, wherein X is Cl, Br or I), a tris(trifluoromethylsulfonyl)carbon acid group, a trifluoromethylsulfonate group, a dicyanamide group, an acetate group ($CH_3COO$), a haloacetate group (($CX_nH_{3-n}$)COO, wherein X is F, Cl, Br, or I, and n is 1, 2 or 3), and a tetraphenylborate group ($BPh_4$) and a derivative thereof ($B(Aryl)_4$, wherein Aryl is a substituted phenyl group) is added into the system, so that an anion exchange reaction occurs, to produce a precipitate of another ionic organic compound.

The heating and reflux time may be from about 5 to about 30 minutes after the addition of the aqueous ammonium salt solution. The thus-precipitated ionic organic compound having an ionic oligomer structure can be easily separated by filtration, and thus any other purification operation is not essential.

The ionic organic compound of the present invention represented by formula (I) can be obtained in the form of an oligomer in which n is from 2 to 30. A mixture of a linear (acyclic) compound with an open structure and a cyclic compound with a closed structure may be obtained, depending on the reaction conditions. While these compounds may be separated from one another as needed, they may be used as a gelling agent in the form of a mixture without being separated from one another. When the mixture is used, the mixing ratio between the cyclic and acyclic compounds may be freely changed.

The chemical structure of the ionic organic compound represented by formula (I) of the present invention includes: the A moiety, such as pyridinium, which is responsible for the solubility in water due to its ionic properties; the B moiety located in the main chain, such as an amide group, which can accelerate a self-organizing phenomenon (aggregation) necessary for gelation by causing intermolecular interaction through hydrogen bonding so that it can finally form a gel; and the C moiety, such as a benzene ring, which can accelerate aggregation by hydrophobic interaction and the affinity between the aromatic rings. These functional groups all have stability under acidic conditions.

With these features, the ionic organic compound of the present invention has a good ability to form a gel with water and is useful as a hydrogel-forming agent for setting water with a very small component ratio, and specifically useful as a water-retaining agent for greening deserts, retaining water in plant culture soil, or the like, as a water-absorbing agent for urine absorption in pet litters, moisture absorption in sanitary products, or the like, or as a moisturizing agent in the field of fine chemical industry, pharmaceuticals, cosmetics, or the like. The compound is stable under acidic conditions and thus can also be used for acid catalysts in setting aqueous acidic solutions and in organic reactions. The gelling agent has a charged electrolyte structure and thus can also be used to form an electrolyte gel in the field of electronic materials.

The hydrogel produced from the ionic organic compound of the present invention can exhibit specific behavior not found in conventional hydrogels, in which even through the structure of the hydrogel is temporarily broken by the application of a pressure such as a mechanical distortion, it can recover its original state in a short period of time and return to a gel with the original mechanical strength.

For example, it has been found that when a 100% distortion is applied to the hydrogel produced from the ionic organic compound of the present invention by shearing with a dynamic viscoelasticity measuring system so that a quasi-liquid state is produced by the mechanical destruction of the gel structure, and then followed by the release of the distortion, the gel can recover its original storage modulus in a very short time of several seconds to several minutes and rapidly return to the quasi-solid state. Even through this distortion applying test is continuously repeated, the rapid return behavior is not lost.

Based on the above characteristics, therefore, the hydrogel of the present invention is promising as a shock absorber, a base material for soft actuators, and an agent for controlling paint material running.

When the ionic organic compound of the present invention is dissolved in a various types of ionic liquid at high temperature with no solvent as a medium and allowed to stand at room temperature, the ionic liquid can be converted into a quasi-solid with a very small component ratio. Thus, the ionic organic compound of the present invention is useful as an ionic liquid-gelling agent.

The ionic liquid gel produced from the ionic organic compound of the present invention can have properties not found in conventional ionic liquid gels, in which the ionic liquid with high electrical conductivity can be converted into a quasi-solid while its properties is substantially maintained (85% or more of the ionic conductivity before the gelation can be maintained) so that the electrical conductivity can change very little before and after gelation. The ionic liquid gel of the present invention is useful as a quasi-solid prevented from causing the problem of leakage or the like for lithium ion batteries practically using ionic liquid, can be used for various sensors with electrodes immersed therein or used as a new solid electrolyte material, and can also be expected to be applied to a new chemical reaction site for organic synthetic reactions in a gel state and the like.

Such an ionic liquid can be obtained, for example, by a process including using the ionic organic compound of the present invention as a gelling agent, dissolving it in an ionic liquid at a high temperature of 80° C. to 300° C., preferably of 120° C. to 200° C., and then allowing the solution to stand at room temperature. The gelling agent may be used in an amount of 5 g/L to 100 g/L to the ionic liquid, preferably of 10 g/L to 80 g/L to the ionic liquid.

The ionic liquid for use in the ionic liquid gel of the present invention may be any type of known ionic liquid with no particular limitation. Specific examples thereof may comprise a cation represented by any of formulae (B1) to (B4) below and an anion ($X^-$).

[Formula 4]

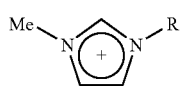
(B1)

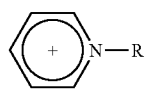
(B2)

-continued

   (B3)

   (B4)

In formulae (B1) to (B4), R represents an alkyl group of 8 or less carbon atoms, particularly preferably of 2 to 4 carbon atoms, which may contain an ether bond. In formulae (B3) and (B4), n is an integer of 1 to 4.

Specifically, examples of the anion (X⁻) for these ionic liquids include an atom or ion selected from a halogen atom (such as F, Cl, Br, and I), a tetrafluoroborate group ($BF_4$), a hexafluorophosphate group ($PF_6$), bis(trifluoromethanesulfonyl)imide, thiocyanate (SCN), a nitrate group ($NO_3$), a sulfate group ($SO_4$), a thiosulfate group ($S_2O_3$), a carbonate group ($CO_3$), a hydrogencarbonate group ($HCO_3$), a phosphate group, a phosphite group, a hypophosphite group, any halogen oxide acid group (such as $XO_4$, $XO_3$, $XO_2$, and XO, wherein X is Cl, Br or I), a tris(trifluoromethylsulfonyl)carbon acid group, a trifluoromethylsulfonate group, a dicyanamide group, an acetate group ($CH_3COO$), a haloacetate group (($CX_nH_{3-n}$)COO, wherein X is F, Cl, Br, or I, and n is 1, 2 or 3), and a tetraphenylborate group ($BPh_4$) and a derivative thereof ($B(Aryl)_4$, wherein Aryl is a substituted phenyl group).

In the chemical structure of the ionic organic compound represented by formula (I) above according to the present invention, the A moiety such as pyridinium is responsible for solubility in water due to its ionic properties. In addition, the positive charge on the pyridinium moiety can easily interact with the surface of carbon nanotubes by a strong affinity known as "cation/π interaction." Thus, the compound can be used as an amphiphilic compound to efficiently disperse carbon nanotubes in a solvent.

The B moiety, such as an amide group, that locates in the main chain of the ionic organic compound can accelerate a self-organizing phenomenon (aggregation) necessary for gelation by causing intermolecular interaction through hydrogen bonding, so that it can finally form a gel in which a solution is set. The C moiety such as a benzene ring can also accelerate aggregation by hydrophobic interaction.

With these features, the ionic organic compound of the present invention is useful as a carbon nanotube-dispersing agent, because it allows uniform dispersion of carbon nanotubes in water, whose load on the environment is low, without the use of any high environmental-load solvent such as an organic solvent, and it allows gelation thereof.

In this case, the ionic organic compounds each may be used singly or as a mixture of two or more kinds thereof.

The carbon nanotube-dispersed liquid or gel produced with the dispersing agent can have high electrical conductivity and good semiconducting properties and thus can be expected to be applied to or developed for intelligent materials for electric actuators and the like.

Furthermore, the dispersion liquid or gel described above can easily form a carbon nanotube-containing thin film, the thickness of which can also be readily and uniformly controlled and provided. An electron emission device using carbon nanotubes as an electron emission source or a light-emitting material using carbon nanotubes as an emitter can also be obtained therewith.

The carbon nanotube-dispersed liquid of the present invention preferably contains a carbon nanotube-dispersing agent composed of the ionic organic compound, carbon nanotubes, and a solvent including at least water, and may be prepared by adding the carbon nanotube-dispersing agent in an amount of less than 1% by weight to the solvent. The lower limit of the amount may be, but not limited to, 0.01% by weight or more, so that favorable dispersing effects can be exhibited. If the amount of the addition of the carbon nanotube-dispersing agent is 1% by weight or more to the solvent, the resultant dispersion liquid may be set to form a carbon nanotube-dispersed gel as described later.

The carbon nanotubes to be used may be either single-walled carbon nanotubes or multi-walled carbon nanotubes and may have general sizes such as several nm to hundreds nm in diameter and several nm to several μm in length. In view of the effects of the dispersion properties, or electrical conductivity or thermal conductivity of carbon nanotubes, single-walled carbon nanotubes are particularly preferably used. The carbon nanotubes for use in the present invention may be generally known carbon nanotubes and may be produced by known conventional methods.

With respect to the amount to be added of the carbon nanotubes, for example, single-walled carbon nanotubes may be added in an amount of up to about 0.3% by weight to the solvent, so that they can be favorably dispersed. Particularly preferably, the amount is desirably from 0.001 to 0.1% by weight to the solvent.

The solvent for the carbon nanotube-dispersed liquid is one that contains at least water, and, if necessary, may be a mixed solvent containing, in addition to water, a water-soluble organic solvent, for example, various alcohols, such as methanol, ethanol, propanol, and isopropanol; ketones, such as acetone; dimethylsulfoxide, N,N-dimethylformamide, and N-methylpyrrolidone, with no particular limitation to the mixing ratio of those. In view of the dispersibility of carbon nanotubes, the solvent is preferably pure water deionized.

The carbon nanotube-dispersed liquid according to the present invention can be obtained, for example, by a process including dissolving the carbon nanotube-dispersing agent at a given concentration in the solvent at high temperature, adding carbon nanotubes thereto, and having the resultant liquid be irradiated with ultrasonic waves. A commercially available ultrasonic cleaner, for example, with a power of 130 W and a frequency of 35 kHz may be used for ultrasonic waves. A good dispersing effect can be obtained by ultrasonic treatment for about 1 hour. The ultrasonic conditions are not limited to those, and the power, frequency and irradiation time may be appropriately determined, depending on the blending ratio of each component to be contained in the dispersion liquid.

The carbon nanotube-dispersed gel of the present invention contains a solvent containing at least water, and a carbon nanotube-dispersing agent composed of any of the above ionic organic compounds. The carbon nanotube-dispersing agent is preferably added in an amount of at least 1% by weight to the solvent, and the upper limit thereof is preferably 10% by weight or less, in view of the dispersibility of carbon nanotubes in the solvent.

The carbon nanotube-dispersed gel may be produced by evaporating the solvent from the carbon nanotube-dispersed liquid in such a manner that the content of the carbon nanotube-dispersing agent would be at least 1% by weight to the solvent. Alternatively, the carbon nanotube-dispersed gel may be directly prepared by adding the carbon nanotube-dispersing agent in an amount of at least 1% by weight to the solvent.

The solvent, the carbon nanotubes, the addition amount thereof, the ultrasonic wave irradiation, and the like, for the carbon nanotube-dispersed gel of the present invention are the same as those for the above-described carbon nanotube-dispersed liquid, and the descriptions thereof are omitted.

The carbon nanotube-containing thin film of the present invention can be easily obtained by spreading (applying) the carbon nanotube-dispersed liquid or carbon nanotube-dispersed liquid gel on a substrate, and drying the resultant substrate.

The method for spreading it on the substrate is preferably, but not limited to, a casting method or a spin coating method. The substrate to be used is generally, but not limited to, a quartz substrate. Even after the thin film is formed, the carbon nanotubes are dispersed in the resulting thin film in such a manner that they are separated from one another.

The carbon nanotube-containing thin film produced as described above may be used as a light-emitting material in which the carbon nanotubes serve as an emitter.

EXAMPLES

The present invention will be described in more detail based on examples and the like given below, but the present invention is not meant to be limited by these examples.

Example 1

Synthesis of Ionic Organic Compounds from Amines and Acid Chlorides 4.27 g (45.3 mmol) of 4-aminopyridine and 8.34 g (45.3 mmol) of 4-(chloromethyl)benzoic acid chloride were mixed in 100 mL of anhydrous dichloromethane, in the presence of 6.95 mL (49.9 mmol) of triethylamine, and followed by stirring at room temperature overnight, to form white precipitate. The resultant precipitate was separated by filtration, to give 9.51 g of the ionic organic compound 1•Cl represented by formula (1) below in which X is a chloride ion. The yield was 85%. The structural formula of the product and the synthetic reaction are represented by the formulae below.

[Formula 5]

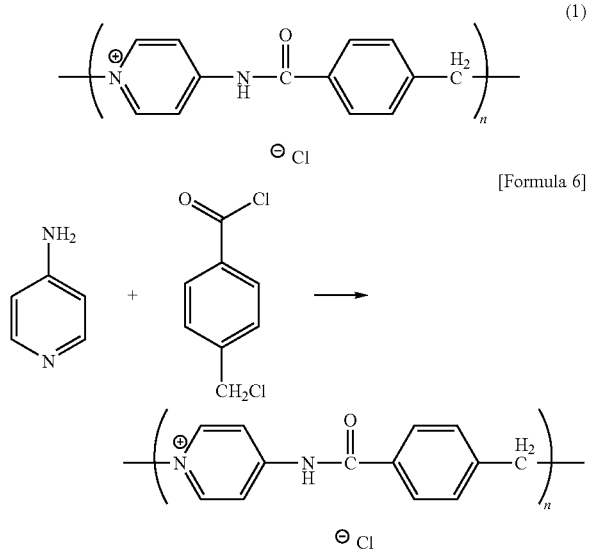

This ionic organic compound includes the positively charged pyridinium ring, the hydrogen-bondable amide group, and the benzyl moiety bonded on the nitrogen in the pyridinium ring, which are recognized to correspond to A, B and C, respectively, in the above-shown formula. X is an anion of a chloride atom. As a result of mass spectrometry, n and m each were an integer of 2 to 30. A hydrogel can be easily synthesized (see FIG. 1), by drying the ionic organic compound under vacuum, and then dissolving the thus-dried product in an aqueous solution at high temperature, and allowing the resultant solution to stand at room temperature.

Figure 2:
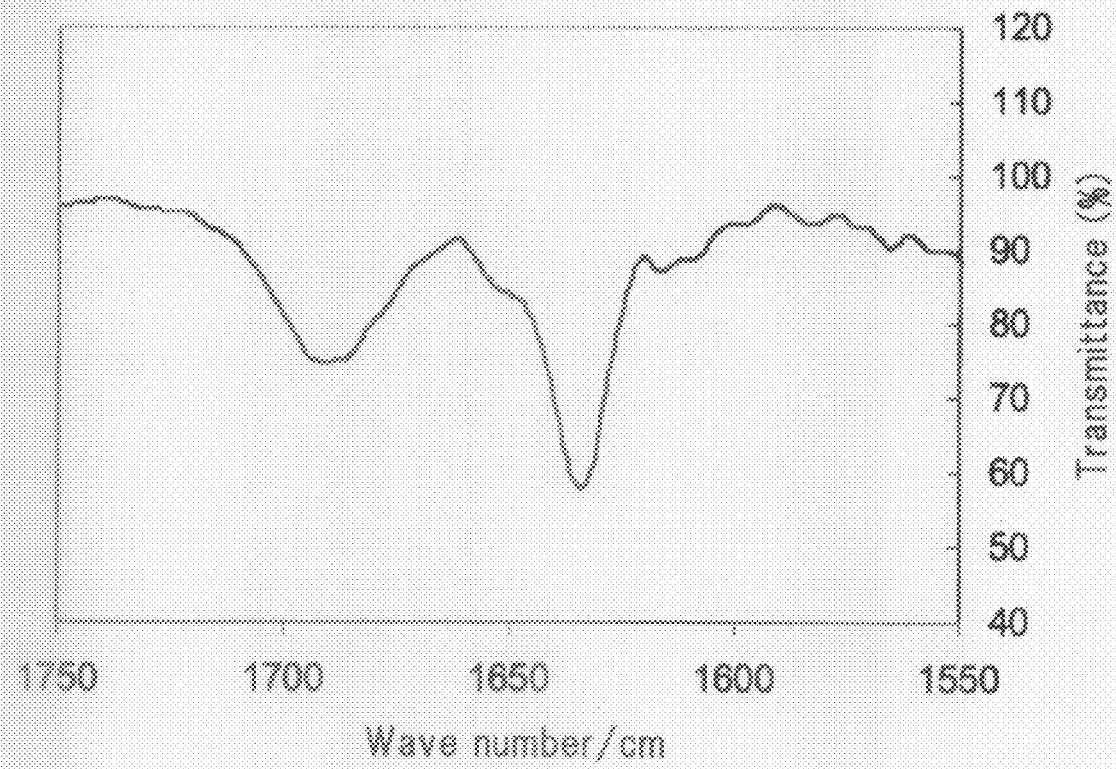
FIG. 2 is an IR spectrum of the hydrogel prepared using the ionic organic compound 1•Cl of the present invention as a gelling agent (vertical axis: transmittance, horizontal axis: cm$^{-1}$).

The chemical structure of the resulting ionic organic compound 1•Cl was identified by observing a methylene peak (at about 6 ppm) that was shifted to the low magnetic field side and characteristic of the benzylpyridinium salt forming a partial structure of the gelling agent, by $^1$H-NMR of a dilute solution (heavy water). Further, in the IR spectrum of a hydrogel prepared with heavy water, two stretching vibrations due to free carbonyl and hydrogen bonding were observed at 1691 cm$^{-1}$ and 1635 cm$^{-1}$, respectively, as shown in FIG. 2.

The NMR data (300 MHz, D$_2$O) of the ionic organic compound 1•Cl: δ 5.83 (Ph-CH$_2$—N$^+$, 2H), 7.66 (2H), 8.05 (2H), 8.31 (2H), 8.77 (2H).

It is assumed that the benzoic acid amide compound represented by formula (2) below be first produced as an intermediate in the reaction system, and then quaternarized and self-condensed, to form the ionic organic compound 1•Cl.

[Formula 7]

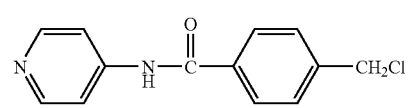

The compound of formula (2) is extremely reactive and thus difficult to isolate. However, since the formation of the pyridinium salt (3) represented by the following structural formula was observed when the synthesis was performed under the conditions free from triethylamine (which is a hydrogen chloride-trapping agent), the coupling reaction (amidation reaction) at the first stage by amidation was confirmed.

[Formula 8]

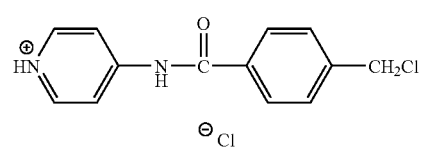

The NMR data (300 MHz, MeOH-d$_4$) of the pyridinium salt of formula (3): δ 4.64 (Ph-CH$_2$—Cl, 2H), 6.87 (d, 2H), 7.46 (d, 2H), 7.91 (d, 2H), 8.00 (d, 2H).

A derivative in which X was a bromide anion was synthesized by the same reaction, except that 4-(bromomethyl)benzoic acid bromide was used as the acid halide.

A group of ionic organic compounds represented by any of formulae (4) to (14), were synthesized from the corresponding amines and the corresponding acid chloride compounds, by using the reaction similar to the above amidation followed by quaternarization and self-condensation. The results are shown below.

[Formula 9]

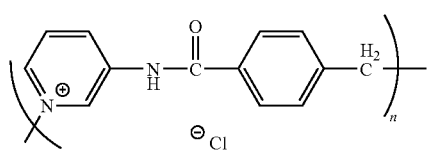

(4)

The NMR data (300 MHz, D$_2$O) of the ionic organic compound 4·Cl: δ 6.00 (brs, 2H), 7.76 (m, 2H), 8.16 (m, 3H), 8.73 (m, 1H), 8.88 (m, 1H), 9.71 (brs, 1H).

[Formula 10]

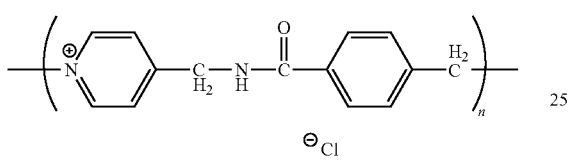

(5)

The NMR data (300 MHz, MeOH-d$_4$) of the ionic organic compound 5·Cl: δ 4.63 (m, 2H), 5.90 (brs, 2H), 7.60 (m, 2H), 8.10 (m, 4H), 9.00 (m, 2H).

[Formula 11]

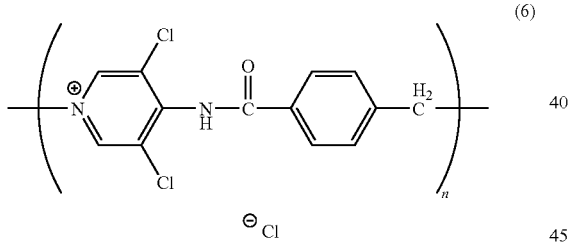

(6)

The NMR data (300 MHz, DMSO-d$_6$) of the ionic organic compound 6·Cl: δ 5.54 (brs, 2H), 7.60 (m, 2H), 8.05 (m, 2H), 8.90 (m, 2H), 9.06 (m, 2H).

[Formula 12]

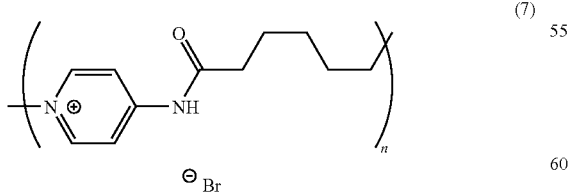

(7)

The NMR data (300 MHz, MeOH-d$_4$) of the ionic organic compound 7·Br: δ 1.47 (m, 2H), 1.78 (m, 2H), 2.02 (m, 2H), 2.57 (m, 2H), 4.48 (t, N(+)—CH$_2$—, 2H), 8.17 (m, 2H), 8.73 (m, 2H).

[Formula 13]

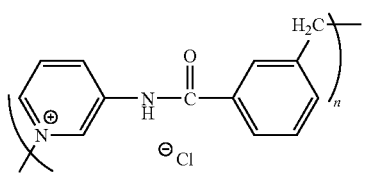

(8)

[Formula 14]

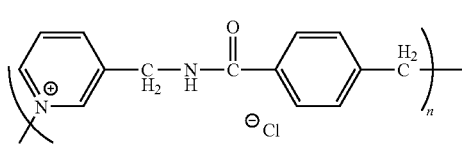

(9)

[Formula 15]

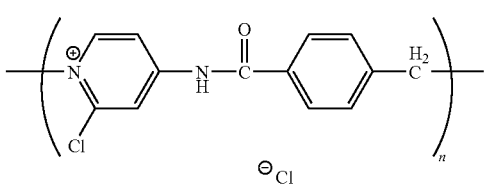

(10)

[Formula 16]

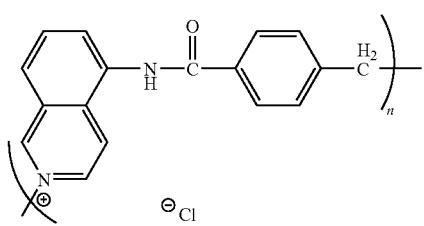

(11)

[Formula 17]

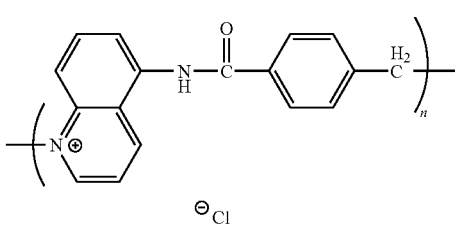

(12)

[Formula 18]

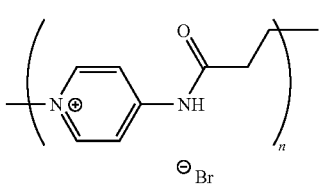

(14)

-continued

[Formula 19]

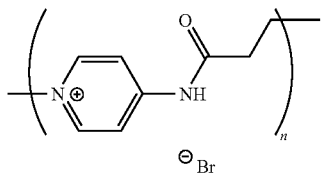

(14)

Example 2

Synthesis of Ionic Organic Compounds from Amines and Isocyanate Compounds 4-aminopyridine (0.562 g, 5.97 mmol) and 4-chloromethylbenzoic acid isocyanate (1.00 g, 5.97 mmol) were mixed in 100 mL of anhydrous tetrahydrofuran (THF), and followed by stirring under heating overnight. After the reaction, white precipitate was produced, and separated by filtration, to give 1.56 g of an ionic organic compound (Product 15) as white powder. The yield of the ionic organic compound (15) (ionic organic compound 15•Cl), in which X is chlorine, was quantitative (100%). The structural formula of the product and the synthetic reaction are represented by the formulae below.

[Formula 20]

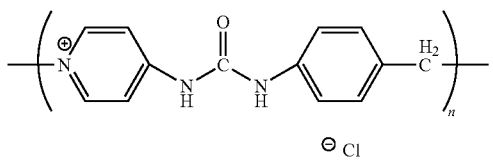

(15)

[Formula 21]

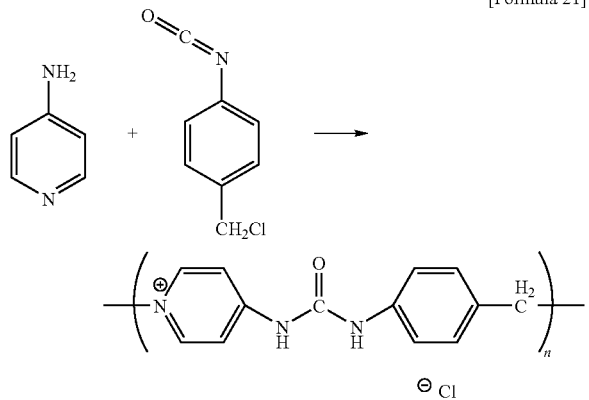

This ionic organic compound 15•Cl includes the positively charged pyridinium ring, the hydrogen-bondable urea group, and the benzyl moiety bonded on the nitrogen in the pyridinium ring, which are recognized to correspond to A, B and C, respectively, in the above-shown formula. X is a chlorine atom. As a result of mass spectrometry, n and m each were an integer of 2 to 30. A hydrogel can be easily synthesized, by drying the ionic organic compound under vacuum, and then dissolving the thus-dried product in an aqueous solution at high temperature, and allowing the resultant solution to stand at room temperature.

In addition, the chemical structure of the ionic organic compound 15•Cl was identified, by observing a methylene peak (at about 5.4 ppm) that was shifted to the low magnetic field side and characteristic of the benzylpyridinium salt forming a partial structure of the gelling agent, by $^1$H-NMR in heavy water.

The NMR data (300 MHz, D$_2$O) of the ionic organic compound 15•Cl: δ 5.3 (Ph-CH$_2$—N$^+$, 2H), 6.9 (2H), 7.5 (2H), 8.0 (2H), 8.5 (2H).

It is assumed that the benzoic acid urea compound represented by structural formula (16) below be first produced as an intermediate in the reaction system and then cause a quaternarization reaction between the molecules thereof to be ionically self-condensed, to form the ionic organic compound 15•Cl.

[Formula 22]

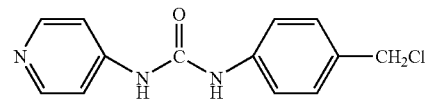

(16)

A derivative in which X was a bromide anion was synthesized by the same reaction, except that 4-bromomethylbenzoic acid bromide was used as the acid halide.

Furthermore, the derivative of formula (17) was synthesized in a similar manner using the quaternarization and self-condensation reaction of the corresponding amine and the corresponding isocyanate.

[Formula 23]

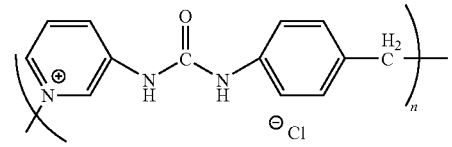

(17)

The NMR data (300 MHz, DMSO-d$_6$) of the ionic organic compound 17•Cl: δ 5.81 (brs, 2H), 7.55 (m, 4H), 8.05 (m, 1H), 8.30 (m, 1H), 8.73 (m, 1H), 9.40 (m, 1H), 10.10 (br, 1H), 10.80 (br, 1H).

Furthermore, the ionic organic compound (18) shown below having a urethane bond moiety was synthesized in a similar manner by the reaction of 4-hydroxypyridine and an isocyanate.

[Formula 24]

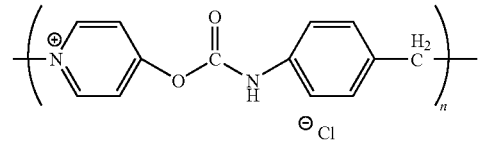

(18)

Example 3

Preparation of Hydrogel 1

The ionic organic compound 1•Cl represented by formula (1) was mixed with neutral water so that the concentration of the compound would be about 1% by weight, and followed by heating, to make the solution become clear near 80° C. to give a homogeneous colorless solution. The resultant solution was allowed to stand at the room temperature for cooling for about 5 minutes, to form a stable translucent hydrogel, as shown in FIG. 1. The gelation process was easily determinable with a glass sample tube. Specifically, the gelling agent was mixed with water in the sample tube at a concentration of about 1% by weight, heated to form a homogeneous solution and then cooled at room temperature. When the falling of the liquid was not observed in the sample tube turned upside down, it was judged that a gel state was occurred. The critical gelation concentration is 7.5 g/L at room temperature in neutral water, and the gelation is possible at or above that concentration.

Figure 3:
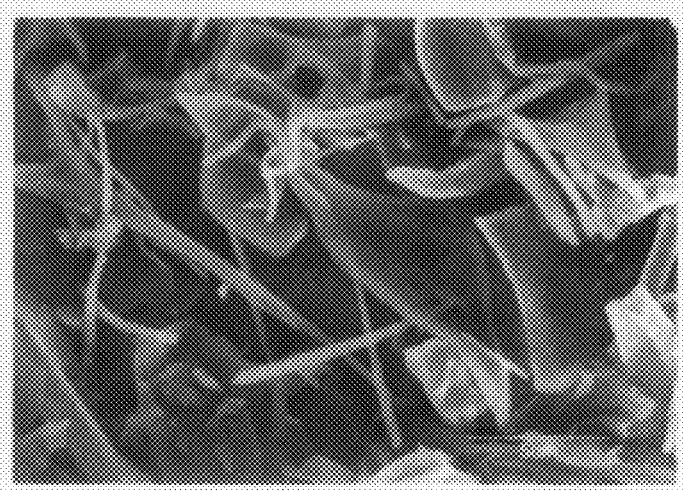
FIG. 3 is an SEM photograph of a xerogel after lyophilization of the hydrogel prepared using the ionic organic compound 1 •Cl of the present invention as a gelling agent (the length of a white scale at the lower right portion is 5 μm).

Using a method similar to the above, it was confirmed that gelation of an acidic solution was also possible. Specifically, as shown in Table 5, gelation was also observed in a 0.1-N hydrochloric acid solution and in a 45% by weight phosphoric acid solution. The thus-prepared hydrogel (neutral) was lyophilized to form a xerogel. In an SEM photograph of the xerogel (see FIG. 3), a fine sheet-like structure was observed. This suggests that the gelation may be induced by lamellar aggregation of the ionic organic compound 1•Cl (gelling agent). Table 1 provides a summary of various gelation conditions in the case where the gelling agent was used at a concentration of 1% by weight.

TABLE 5

| | HCl aqueous solution | | | $H_3PO_4$ aqueous solution | | |
|---|---|---|---|---|---|---|
| $H_2O$ | 0.01 N | 0.1 N | 1 N | 40 wt % | 45 wt % | 50 wt % |
| G | G | G | I | G | G | S |

HCl concentration, normality;
phosphoric acid concentration, % by weight;
G, gelation,
I, insoluble,
S, solution

Example 4

Preparation of Hydrogel 2

Figure 4:
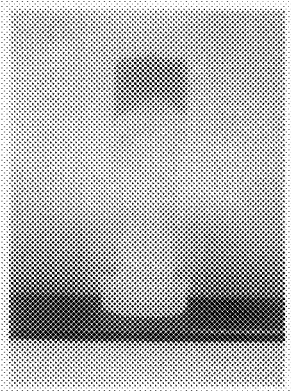
FIG. 4 is a photograph of a hydrogel in a sample tube, which is prepared using an ionic organic compound 1•Cl of the present invention as a gelling agent.

A similar gelling function was also observed when another ionic organic compound 15•Cl was used. Specifically, the ionic organic compound 15•Cl having the urea group in its molecule was mixed with neutral water so that the concentration of the compound would be about 1% by weight, and followed by heating, to make the solution become clear near 80° C. to form a homogeneous yellow solution. The resultant solution was allowed to stand at the room temperature for cooling for about 5 minutes, to form a stable hydrogel, as shown in FIG. 4. The gelation process was easily determinable with a glass sample tube. Specifically, the ionic organic compound 15•Cl (gelling agent) was mixed with water in the sample tube at a concentration of about 1% by weight, heated to form a homogeneous solution and then cooled at room temperature. When the falling of the liquid was not observed in the sample tube turned upside down, it was judged that a gel state was occurred.

Figure 5:
FIG. 5 is an SEM photograph of a xerogel after lyophilization of the hydrogel prepared using the ionic organic compound 15•Cl of the present invention as a gelling agent (the length of a white scale at the lower right portion is 2 μm).

Using a method similar to the above, it was confirmed that gelation of an acidic solution (with an acidity of about 1) was also possible. Specifically, gelation of a solution was also observed in a 0.1-N hydrochloric acid solution and in a 45% by weight phosphoric acid solution. The thus-prepared hydrogel (neutral) was lyophilized to form a xerogel. In an SEM photograph of the xerogel (see FIG. 5), a fine structure was observed. This suggests that the gelation may be induced by lamellar aggregation of the ionic organic compound 15•Cl, which is a gelling agent.

Example 5

Evaluation of Hydrogel Rheology: High-Speed Viscoelasticity-Recovering Properties The ionic organic compound 1•Cl and deionized pure water were utilized, to form a dispersion liquid in which the ionic organic compound 1•Cl was dispersed at a concentration of 30 g/L. The dispersion liquid was heated to form a homogeneous transparent solution, and then allowed to stand at room temperature, to form a white hydrogel. The dynamic viscoelasticity of this hydrogel was measured at 25° C.

Figure 6:
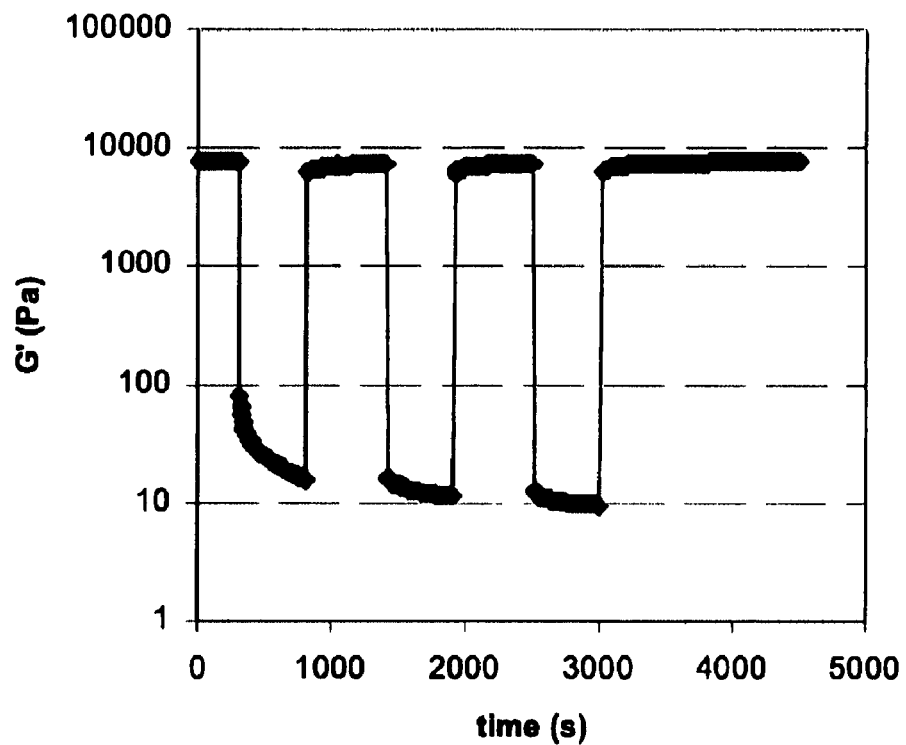
FIG. 6 shows changes in storage modulus (G') with the lapse of time in the continuous distortion application measurement of Example 5 (a: a graph of absolute values of storage modules, b: a graph of recovery rate ($G'/G_0'$))
Figure 6:
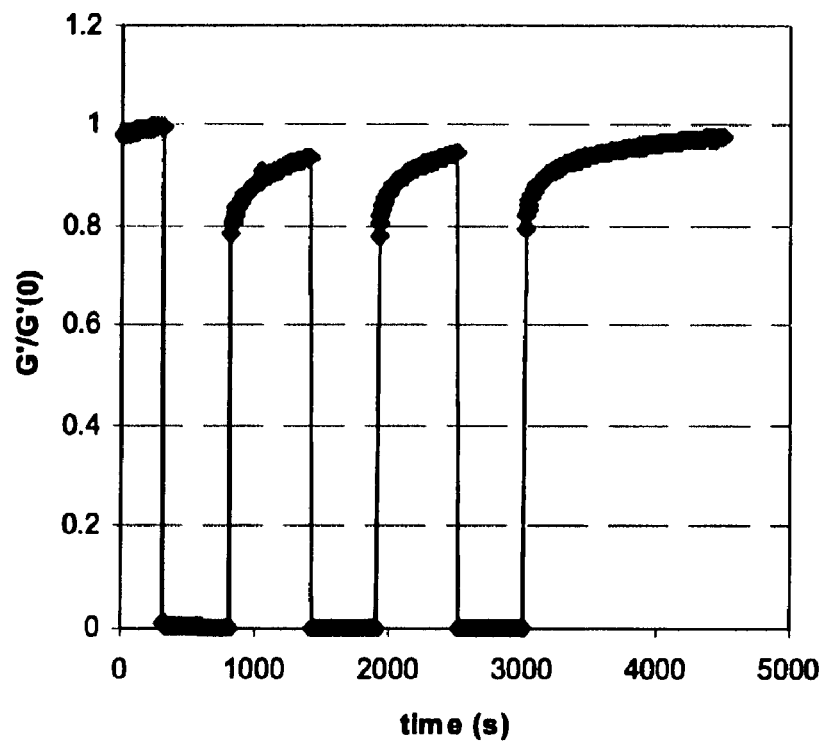

Under the conditions of frequency 6 rad/s and distortion 0.02%, the values of physical properties resulting from the measurement were a storage modulus ($G_0'$) of about 8,000 Pa and a loss tangent (tanδ) of about 0.1, which indicated quasi-solid properties (see FIG. 6a). The application of 100% distortion to the gel with the frequency kept at the same level (6 rad/s) reduced the storage modulus (Gs') to about 30 Pa and provided a loss tangent value (tanδ) of 10 or more, which indicated quasi-liquid properties. The 100% distortion load was further continuously applied for 500 seconds, and immediately after that, the distortion was changed to the original value 0.02%, and the dynamic viscoelasticity was measured. As a result, the storage modulus (G') reached about 6,200 Pa after 8 seconds and reached about 7,500 Pa after 600 seconds (10 minutes). These values were each calculated into a storage modulus recovery rate ($G'/G_0'$) relative to the initial value of the storage modulus ($G_0'$). As a result, the value after 8 seconds was 78%, and that after 10 minutes was 94% (see FIG. 6b). The recovery speeds each are a value higher by at least two orders than those in the case of known conventional natural gelling agents such as gelatin, which shows that the speed is one of unique properties of the above-mentioned hydrogel. This high-speed recovery behavior was repeatable. Even when a cycle of a low distortion load (0.02%) and a high distortion load (100%) was continuously repeated tree times, the high-speed viscoelasticity-recovering behavior was not lost (see FIG. 6).

Example 6

Preparation of Ionic Liquid Gel with Ionic Organic Compound 1•Cl

The ionic organic compound 1•Cl can gel a water-soluble ionic liquid (e.g. 1-ethyl-3-methylimidazolium nitrate, or N-butylpyridinium tetrafluoroborate), which is in a state containing water.

The ionic organic compound 1•Cl whose anion was a chloride ion was added to 1-ethyl-3-methylimidazolium nitrate containing 10% of water, so that the concentration of the compound would be 20 g/L, and dissolved under heating at about 100° C. on a hot plate. After the compound was completely dissolved, the solution was allowed to cool at room temperature for about 5 minutes, to form a stable white-turbid ionic liquid gel. Even after the sample was dried in vacuum at 90° C. overnight, the gel state still remained.

In a similar manner, the ionic organic compound 1•Cl was added to N-butylpyridinium tetrafluoroborate containing 20% of water, so that the concentration of the compound would be 20 g/L, and dissolved under heating at about 100° C. on a hot plate. The solution was allowed to cool at room temperature for about 5 minutes, to form a white turbid ionic liquid gel.

Example 7

Synthesis of Ionic Organic Compounds by Anion Exchange Reaction

<Anion Exchange Reaction 1: Synthesis of Ionic Organic Compound 1•PF Having Hexafluorophosphate Ion as Anion X>

To 860 mg of the ionic organic compound 1•Cl with the anion of chlorine, 200 mL of water was added, followed by heating, to make the compound be completely dissolved. To the solution, was added 20 mL of an aqueous solution of 625 mg of ammonium hexafluorophosphate, under reflux under heating. The mixture was then refluxed under heating for 10 minutes. The solution became white and turbid at the moment of the addition. Thereafter, the solution was filtered at the hot state, to give 1.24 g of the desired product ionic organic compound 1•$PF_6$ whose anion was a hexafluorophosphate ion. The yield was almost 100%.

Figure 7:
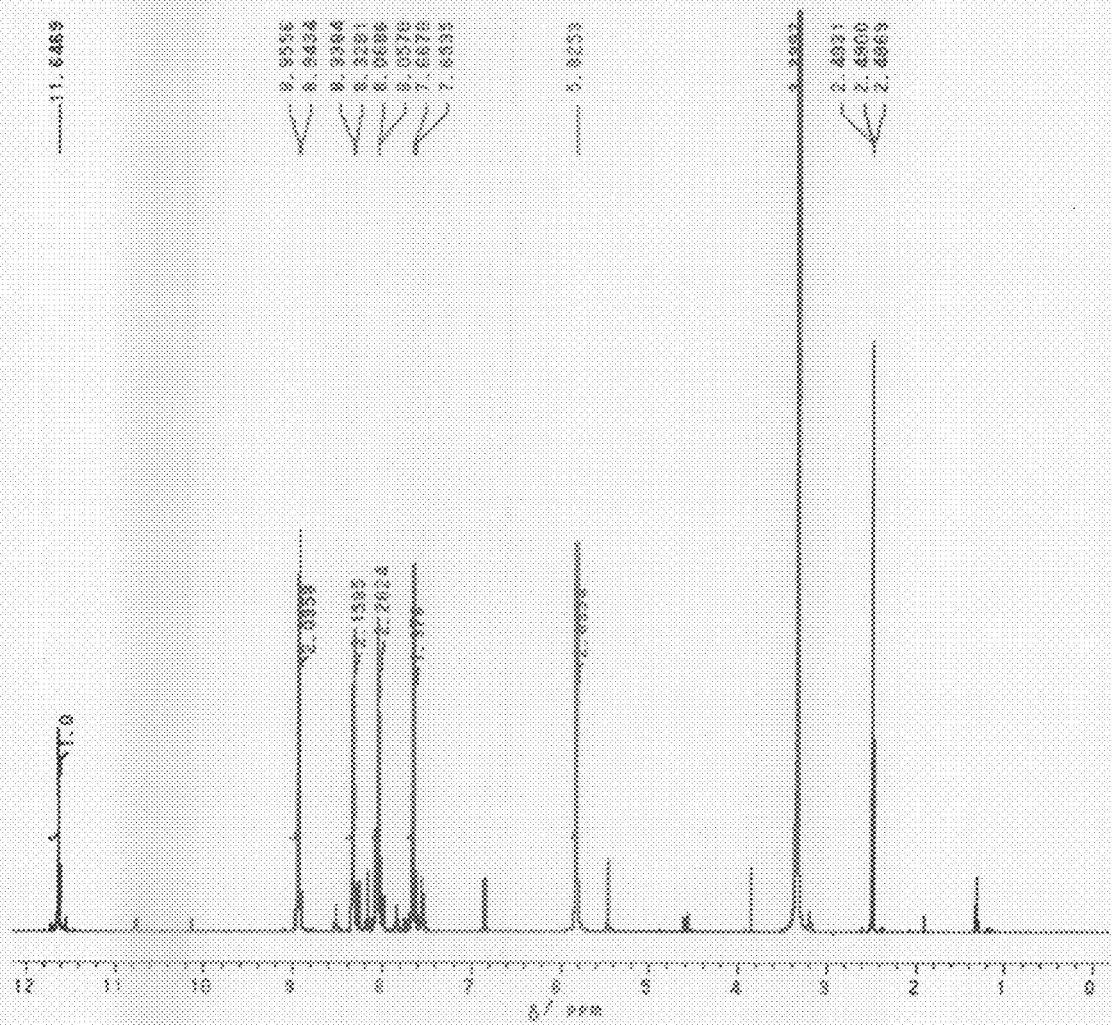
FIG. 7 is a ¹H-NMR spectrum of an ionic organic compound 1•PF$_6$ obtained by an anion exchange reaction 1.

The NMR data (600 MHz, DMSO-$d_6$) of the ionic organic compound 1•$PF_6$: δ 11.65 (NH, 1H), 8.94 (2H), 8.33 (2H), 8.06 (2H), 7.66 (2H), 5.83 ($CH_2$, 2H) (see FIG. 7).

<Anion Exchange Reaction 2: Synthesis of Ionic Organic Compound 1•$BF_4$ Having Tetrafluoroborate Ion as Anion X>

To 150 mg of the ionic organic compound 1•Cl with the anion of chlorine, 25 mL of water was added, followed by heating, to make the compound be completely dissolved. To the solution, was added 20 mL of an aqueous solution of 6.40 g of ammonium tetrafluoroborate, under reflux under heating. The mixture was then refluxed under heating for 3 hours. The solution became white and turbid at the moment of the addition. Thereafter, the solution was filtered at the hot state, to give 155 mg of the desired product ionic organic compound 1•$BF_4$ whose anion was a tetrafluoroborate ion. The yield was 82%.

The NMR data (300 MHz, DMSO-$d_6$) of the resulting ionic organic compound 1•$BF_4$: δ 11.66 (NH, 1H), 8.96 (2H), 8.34 (2H), 8.07 (2H), 7.66 (2H), 5.84 ($CH_2$, 2H).

<Anion Exchange Reaction 3: Synthesis of Ionic Organic Compound 1•TFSI Having Bis(trifluoromethanesulfonyl)imide Ion as Anion X>

To 190 mg of the ionic organic compound 1•Cl with the anion of chlorine, 25 mL of water was added, followed by heating, to make the compound be completely dissolved. To the solution, was added 10 mL of an aqueous solution of 1.11 g of lithium bis(trifluoromethanesulfonyl)imide, under reflux under heating. The mixture was then refluxed under heating for 30 minutes. The reaction liquid was then cooled to room temperature, to form a white solid precipitate. The resultant precipitate was separated by filtration, to give 300 mg of the desired product ionic organic compound 1•TFSI whose anion was a bis(trifluoromethanesulfonyl)imide ion. The yield was 79%.

The NMR data (300 MHz, DMSO-$d_6$) of the ionic organic compound 1•TFSI: δ 11.66 (NH, 1H), 8.96 (2H), 8.34 (2H), 8.07 (2H), 7.67 (2H), 5.84 ($CH_2$, 2H).

<Anion Exchange Reaction 4: Synthesis of Ionic Organic Compound 1•I Having Iodide Ion as Anion X>

To 150 mg of the ionic organic compound 1•Cl with the anion of chlorine, 20 mL of water was added, followed by heating, to make the compound be completely dissolved. To the solution, was added 20 mL of an aqueous solution of 8.81 g of ammonium iodide, under reflux under heating. The mixture was then refluxed under heating for 30 minutes. The reaction liquid was then cooled to room temperature, to form a yellow-colored solid precipitate. The resultant precipitate was separated by filtration, to give 192 mg of the desired product ionic organic compound 1.1 whose anion was an iodide ion. The yield was 93%.

<Anion Exchange Reaction 5: Synthesis of Ionic Organic Compound 1•SCN Having Thiocyanate Ion as Anion X>

To 200 mg of the ionic organic compound 1•Cl with the anion of chlorine, 30 mL of water was added, followed by heating, to make the compound be completely dissolved. To the solution, was added 30 mL of an aqueous solution of 4.10 g of lithium thiocyanate, under reflux under heating. The mixture was then refluxed under heating for 10 minutes. The reaction liquid was then cooled to room temperature, to form a white solid precipitate. The resultant precipitate was separated by filtration, to give 210 mg of the desired product ionic organic compound 1•SCN whose anion was a thiocyanate ion. The yield was 96%.

Example 8-1

Preparation of Ionic Liquid Gel with Ionic Organic Compound 1•$PF_6$

Figure 8:
FIG. 8 shows an ionic liquid gel composed of the ionic organic compound 1•PF$_6$ and an ionic liquid EMIm-BF$_4$, in which gels with concentrations of 20 g/L, 30 g/L and 40 g/L are shown in this order from the left.

A white powder of the ionic organic compound 1•$PF_6$ whose anion was a hexafluorophosphate ion ($PF_6$), as obtained from the anion exchange reaction 1, was added to 1-ethyl-3-methylimidazolium tetrafluoroborate (hereinafter abbreviated to as EMIm-$BF_4$) so that the concentration of the compound would be 20 g/L, followed by heating at about 120° C. on a hot plate to make the compound be dissolved. After the compound was completely dissolved, the resultant liquid was allowed to cool at room temperature for about 5 minutes, to form a stable white turbid ionic liquid gel, as shown in FIG. 8. The critical gelation concentration was 11 g/L at room temperature (about 20° C.). Even when heated to 80° C., the ionic liquid gel prepared at a concentration of 20 g/L maintained the gel state without being broken.

Figure 9:
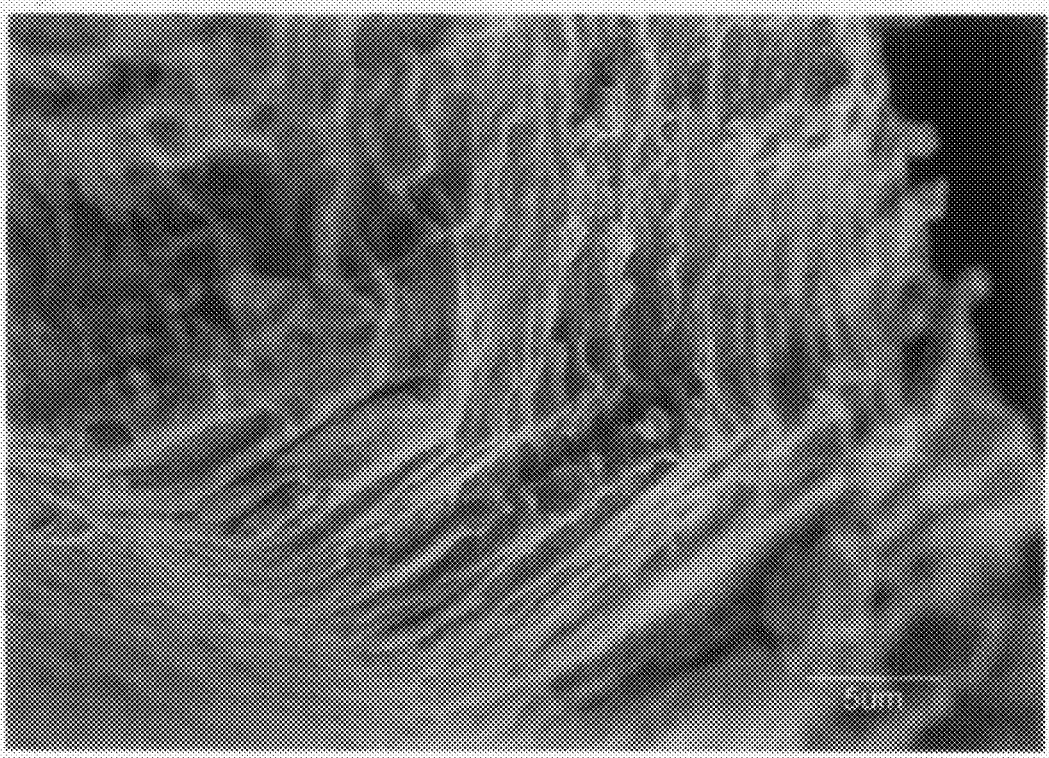
FIG. 9 is an SEM photograph of a residue obtained by washing, with water, the ionic liquid gel prepared with the ionic organic compound 1•PF$_6$ and the ionic liquid EMIm-BF$_4$.

The ionic liquid gel as obtained from the aforementioned reaction was washed with a large amount of water, and then the ionic liquid EMIm-$BF_4$ was removed off by distillation. The residue was separated by filtration. An SEM photograph of the resulting powder revealed the formation of a multilayer (lamellar) structure in which sheet structures were stacked in layers (see FIG. 9). Specifically, it is assumed that in the process of gelation, the ionic organic compound serving as a gelling agent be self-condensed to form sheet-like structures, which gather to form a layered (lamellar) structure, and the ionic liquid serving as a medium be held between the sheet-like structures, so that the solution be prevented from falling in the vessel turned upside down.

In a similar manner, the ionic organic compound 1•$PF_6$ was added to N-butylpyridinium tetrafluoroborate so that the concentration of the compound would be 25 g/L, followed by heating at about 120° C. on a hot plate to make the compound be dissolved. The resultant liquid was allowed to cool at room temperature for about 5 minutes, to form a white turbid ionic liquid gel. The critical gelation concentration was 20 g/L at room temperature (about 20° C.).

Example 8-2

Preparation of Hydrogel with Ionic Organic Compound 1•BF$_4$

A white powder of the ionic organic compound 1•BF$_4$ whose anion was a tetrafluoroborate ion, as obtained from the anion exchange reaction 2, was added to purity water so that the concentration of the compound would be 10 g/L, followed by heating to make the compound be dissolved. After the compound was completely dissolved, the resultant liquid was allowed to cool at room temperature for about 5 minutes, to form a white turbid hydrogel. The critical gelation concentration was 10 g/L. Further, it was also confirmed that gelation was also possible using the 1•BF$_4$ in a dilute solution of sodium hydroxide (concentration 0.01 N), in a dilute solution of hydrochloric acid (concentration 0.5 N), and in an aqueous solution of phosphoric acid (concentration 45% by weight). The critical gelation concentration in those cases was 10 g/L

Example 8-3

Preparation of Ionic Liquid Gel with Ionic Organic Compound 1•TFSI

Figure 10:
FIG. 10 shows an ionic liquid gel composed of the ionic organic compound 1•TFSI and an ionic liquid PP13-TFSI, in which the left shows a lithium salt-containing sample, and the right a lithium salt-free sample, and the concentration of the ionic organic compound 1•TFSI is 40 g/L in both samples.

A white powder of the ionic organic compound 1•TFSI whose anion was a bis(trifluoromethanesulfonyl)imide ion, as obtained from the anion exchange reaction 3, was added to N-methyl-N-propylpiperidinium bis(trifluoromethanesulfonyl)imide (hereinafter abbreviated to as PP13-TFSI) so that the concentration of the compound would be 40 g/L, followed by heating at about 120° C. on a hot plate to make the compound be dissolved. After the compound was completely dissolved, the resultant liquid was allowed to cool at room temperature for about 5 minutes, to form a stable white turbid ionic liquid gel (see FIG. 10).

Further, the gelling agent of the present invention also allows gelation of an ionic liquid that is prepared by adding lithium bis(trifluoromethanesulfonyl)imide salt at a concentration of 10% by weight to PP13-TFSI.

The ionic organic compound 1•TFSI was added to the ionic liquid PP13-TFSI containing the lithium salt at a concentration of 10% by weight, so that the concentration of the compound would be 40 g/L, followed by heating at about 120° C. on a hot plate to make the compound be dissolved. After the compound was completely dissolved, the resultant liquid was allowed to cool at room temperature for about 1 hour, to form a stable white turbid ionic liquid gel (see FIG. 10).

In a similar manner, a white powder of the ionic organic compound 1•TFSI was added to N-methyl-N-propylpyrrolidinium bis(trifluoromethanesulfonyl)imide (hereinafter abbreviated to as PY13-TFSI) so that the concentration of the compound would be 40 g/L, followed by heating at about 120° C. on a hot plate to make the compound be dissolved. After the compound was completely dissolved, the resultant liquid was allowed to cool at room temperature for about 5 minutes, to form a stable white turbid ionic liquid gel.

Example 8-4

Preparation of Organic Gel and Ionic Liquid Gel with Ionic Organic Compound 1•I The ionic organic compound 1•I whose anion was an iodide ion, as obtained from the anion exchange reaction 4, was added to dimethyl sulfoxide (hereinafter abbreviated to as DMSO) so that the concentration of the compound would be 20 g/L, followed by heating to make the compound be dissolved. After the compound was completely dissolved, the resultant liquid was allowed to cool at room temperature for about 5 minutes, to form a yellow turbid organic gel. The critical gelation concentration was 10 g/L.

The ionic organic compound 1•I whose anion was an iodide ion, as obtained from the anion exchange reaction 4, was added to an ionic liquid, 1-ethyl-3-propylimidazolium iodide containing 10% of water or DMSO so that the concentration of the compound would be 20 g/L, followed by heating with a heat gun, to make the compound be completely dissolved. Then, the resultant liquid was allowed to cool at room temperature for about 5 minutes, to form a yellow turbid ionic liquid gel. Furthermore, in this case, it was also confirmed that gelation was possible even when an additive, such as iodine, lithium iodide, or 4-tert-butylpyridine, was added at a certain concentration.

Example 9

Measurement of Electrical Conductivity of Ionic Liquid Gel

Figure 11:
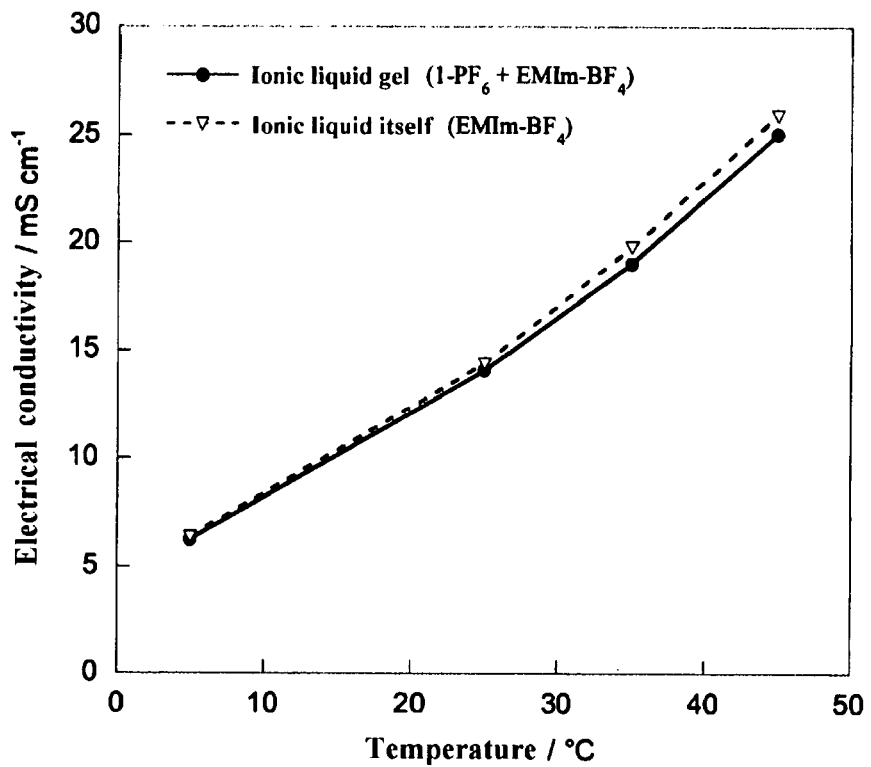
FIG. 11 is a graph showing a comparison between the electrical conductivity of an ionic liquid gel composed of the ionic organic compound 1•PF$_6$ (1•PF$_6$) and the ionic liquid EMIm-BF$_4$ and the electrical conductivity of the ionic liquid EMIm-BF$_4$ itself.

The electrical conductivity of the ionic liquid gel (the ionic organic compound 1•PF$_6$ (1•PF$_6$)+EMIm-BF$_4$) prepared at a concentration of 20 g/L, as shown in Example 8-1, was measured by a complex impedance method, and compared with the electrical conductivity of the ionic liquid EMIm-BF$_4$ itself. The result is shown in Table 6 and FIG. 11. From the result, it is found that the electrical conductivity of the gel was only at most several % lower than that before the gelation in the measurement temperature range (5 to 45° C.) and that also after the gelation, the electrical conductivity little changed.

TABLE 6

| State | Temperature | | | |
|---|---|---|---|---|
| | 5° C. | 25° C. | 35° C. | 45° C. |
| Electrical conductivity A (mS/cm) of ionic liquid (EMIm-BF$_4$) | 6.37 | 14.37 | 19.74 | 25.92 |
| Electrical conductivity A' (mS/cm) of ionic liquid gel (1 · PF$_6$ + EMIm-BF$_4$) and rate of change (A'/A) | 6.24 (0.979) | 14.06 (0.978) | 18.97 (0.961) | 25.06 (0.967) |

Figure 12:
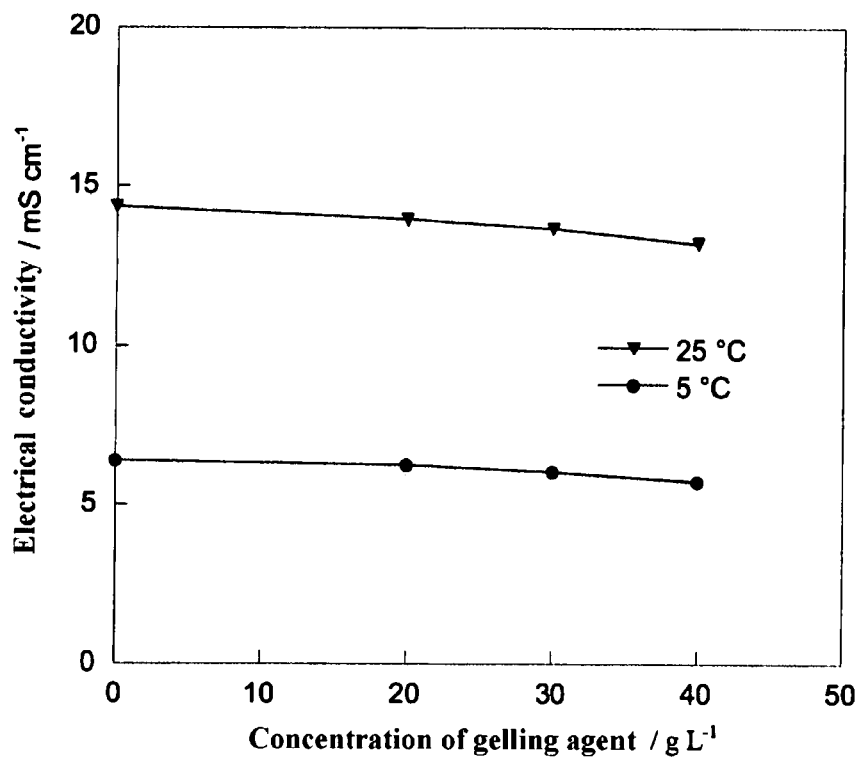
FIG. 12 is a graph showing changes in the electrical conductivity of an ionic liquid gel with different concentrations of the ionic organic compound 1•PF$_6$.

Other ionic liquid gels were also prepared by changing the concentration of the gelling agent to 30 g/L or to 40 g/L, and then measured for electrical conductivity in the same manner by the complex impedance method. The result is shown in Table 7 below and FIG. 12. As a result, although it was observed that the electrical conductivity tended to slightly decrease as the amount of the gelling agent increased, the rate of the decrease was at most only about 10%, which suggests that the ionic conductivity was sufficiently maintained even after a gel in a quasi-solid state was formed.

TABLE 7

| State | Concentration | | | |
|---|---|---|---|---|
| | 0 g/L | 20 g/L | 30 g/L | 40 g/L |
| Electrical conductivity at 5° C. (mS/cm) | 6.37 | 6.24 (0.980) | 6.01 (0.943) | 5.71 (0.896) |
| Electrical conductivity at 25° C. (mS/cm) | 14.37 | 14.06 (0.978) | 13.67 (0.951) | 13.21 (0.919) |

Note:
The parenthesized numbers in the table each indicate a rate of change from the value for 0 g/L as a standard.

Figure 13:
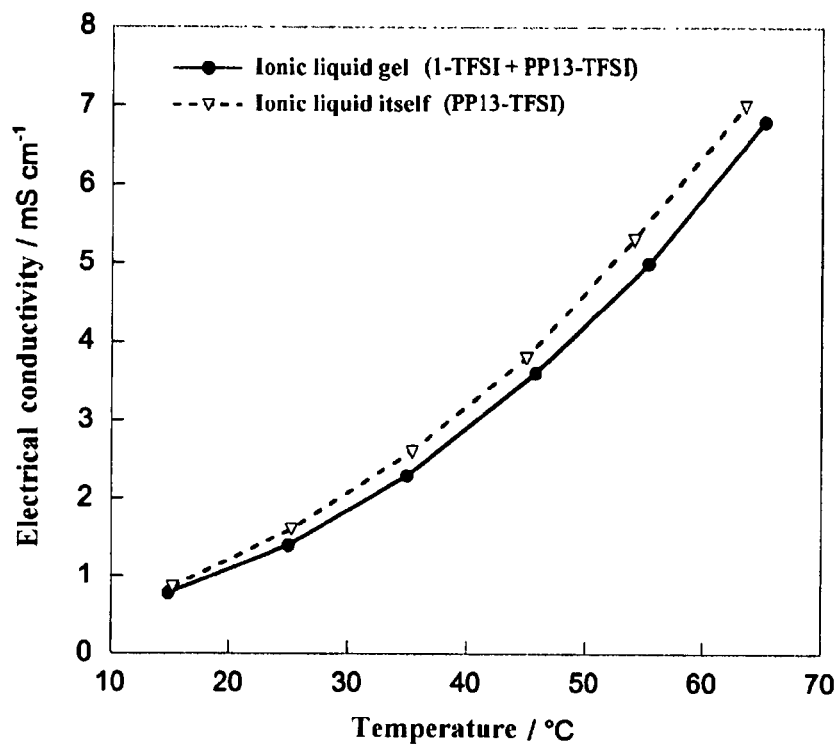
FIG. 13 is a graph showing a comparison between the electrical conductivity of an ionic liquid gel composed of the ionic organic compound 1•TFSI (1•TFSI) and the ionic liquid PP13-TFSI and the electrical conductivity of the ionic liquid PP13-TFSI itself.

The electrical conductivity of the ionic liquid gel (the ionic organic compound 1•TFSI (1•TFSI)+PP13-TFSI) prepared at a concentration of 40 g/L, as shown in Example 8-3, was measured by the complex impedance method, and compared with the electrical conductivity of the matrix ionic liquid PP13-TFSI itself. The result is shown in Table 8 and FIG. 13. As a result, the rate of reduction as compared to the electrical conductivity of the ionic liquid itself was at most about 12%, and it is found that the electrical conductivity was sufficiently maintained in the quasi-solid state in a wide temperature range.

TABLE 8

| | | | | | | |
|---|---|---|---|---|---|---|
| Electrical conductivity A (mS/cm) of ionic liquid (PP13-TFSI) and temperature at measurement (° C.) | 0.85 (15.2) | 1.6 (25.2) | 2.6 (35.4) | 3.8 (45.0) | 5.3 (54.1) | 7.0 (63.5) |
| Electrical conductivity A' (mS/cm) of ionic liquid gel (1 · TFSI + PP13-TFSI) and temperature at measurement (° C.) | 0.77 (14.9) | 1.4 (25.0) | 2.3 (35.0) | 3.6 (45.8) | 5.0 (55.4) | 6.8 (65.2) |
| Rate of change (A'/A) | 0.91 | 0.88 | 0.88 | 0.95 | 0.94 | 0.97 |

Figure 14:
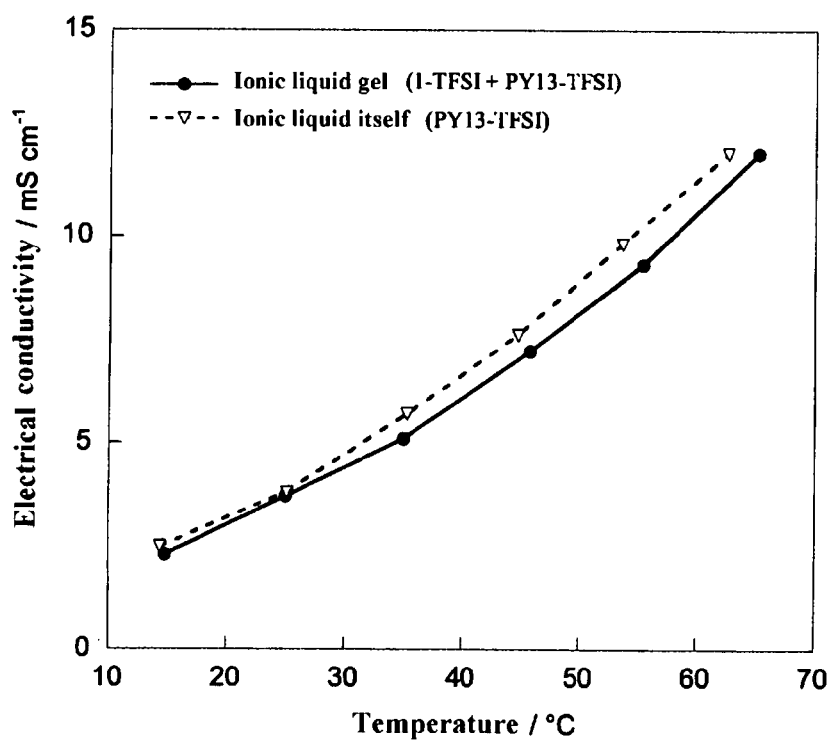
FIG. 14 is a graph showing a comparison between the electrical conductivity of an ionic liquid gel composed of the ionic organic compound 1•TFSI (1•TFSI) and the ionic liquid PY13-TFSI and the electrical conductivity of the ionic liquid PY13-TFSI itself.

Further, the electrical conductivity of the ionic liquid gel (the ionic organic compound 1•TFSI (1•TFSI)+PY13-TFSI) prepared at a concentration of 40 g/L, as shown in Example 8-3, was measured by the complex impedance method, and compared with the electrical conductivity of the matrix ionic liquid PY13-TFSI itself. The result is shown in Table 9 and FIG. 14. Similarly in this case, the rate of reduction as compared to the electrical conductivity of the ionic liquid itself was at most about 11%, and it is found that the electrical conductivity was sufficiently maintained in the quasi-solid state in a wade temperature range.

TABLE 9

| | | | | | | |
|---|---|---|---|---|---|---|
| Electrical conductivity A (mS/cm) of ionic liquid (PY13-TFSI) and temperature at measurement (° C.) | 2.5 (14.4) | 3.8 (25.1) | 5.7 (35.3) | 7.6 (44.7) | 9.8 (53.6) | 12.0 (62.6) |
| Electrical conductivity A' (mS/cm) of ionic liquid gel (1 · TFSI + PY13-TFSI) and temperature at measurement (° C.) | 2.3 (14.8) | 3.7 (25.0) | 5.1 (35.0) | 7.2 (45.8) | 9.3 (55.4) | 12.0 (65.2) |
| Rate of change (A'/A) | 0.92 | 0.97 | 0.89 | 0.95 | 0.95 | 1.00 |

Figure 15:
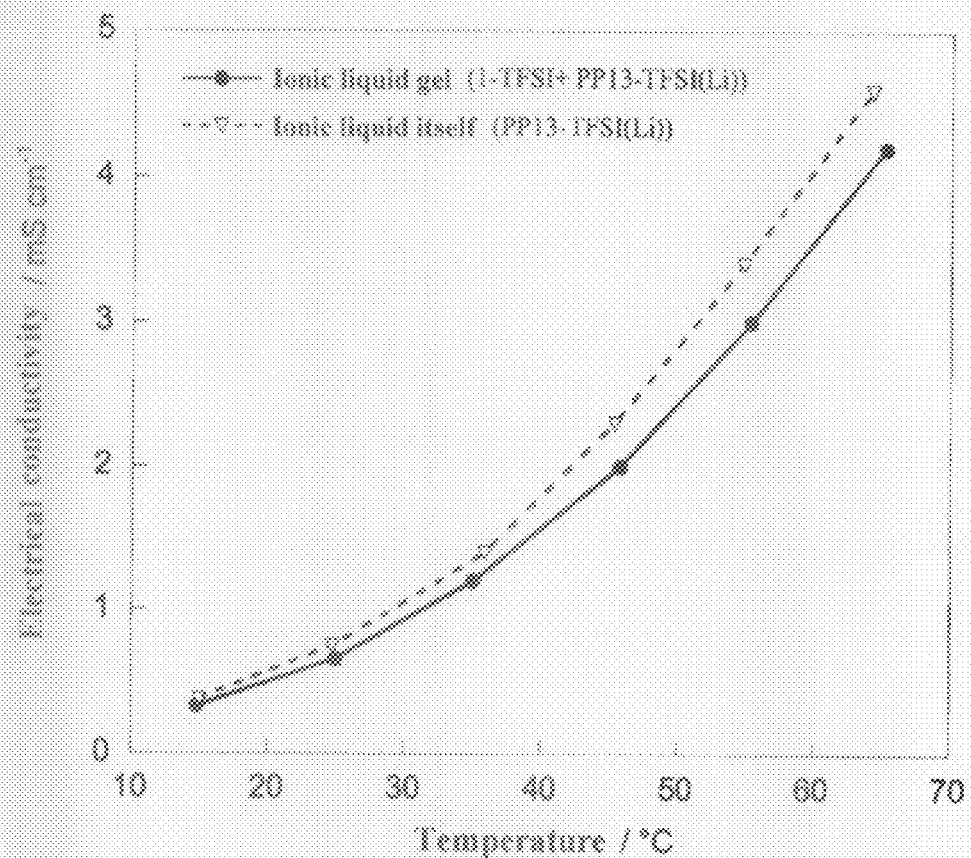
FIG. 15 is a graph showing a comparison between the electrical conductivity of an ionic liquid gel composed of the ionic organic compound 1•TFSI (1•TFSI) and a lithium salt-containing ionic liquid PP13-TFSI (+LiTFSI) and the electrical conductivity of the lithium salt-containing ionic liquid PP13-TFSI (+LiTFSI) itself.

Then, the electrical conductivity of the ionic liquid gel (the ionic organic compound 1•TFSI (1•TFSI)+PP13-TFSI(Li)) prepared under the lithium salt addition conditions, was measured by the complex impedance method, and compared with the electrical conductivity of the gelling agent-free state. The result is shown in Table 10 and FIG. 15. As a result, the rate of reduction as compared with the electrical conductivity of the ionic liquid itself was at most about 14%, and it is found that the electrical conductivity was sufficiently maintained in the quasi-solid state in the presence of the lithium salt additive in a wide temperature range.

TABLE 10

| | | | | | | |
|---|---|---|---|---|---|---|
| Electrical conductivity A (mS/cm) of ionic liquid added with Li (PP13TFSI + LiTFSI(10 wt %)) and temperature at measurement (° C.) | 0.34 (15.0) | 0.75 (24.8) | 1.4 (35.9) | 2.3 (45.4) | 3.4 (54.8) | 4.6 (64.2) |
| Electrical conductivity A' (mS/cm) of ionic liquid gel added with Li (1 · TFSI + PP13-TFSI + LiTFSI(10 wt %)) and | 0.33 (14.9) | 0.66 (25.0) | 1.2 (35.0) | 2.0 (45.8) | 3.0 (55.4) | 4.2 (65.2) |

TABLE 10-continued

| | | | | | | |
|---|---|---|---|---|---|---|
| temperature at measurement (° C.) | | | | | | |
| Rate of change (A'/A) | 0.97 | 0.88 | 0.86 | 0.87 | 0.88 | 0.91 |

Example 10

Figure 16:
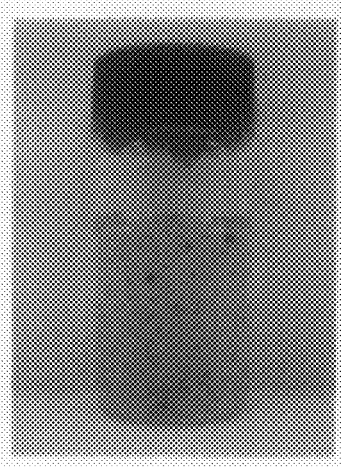
FIG. 16 shows photographs of a single-walled carbon nanotube-dispersed aqueous liquid before and after ultrasonic irradiation in Example 10 ((a), before the irradiation; (b), after the irradiation (irradiation time: 60 minutes)).
Figure 16:
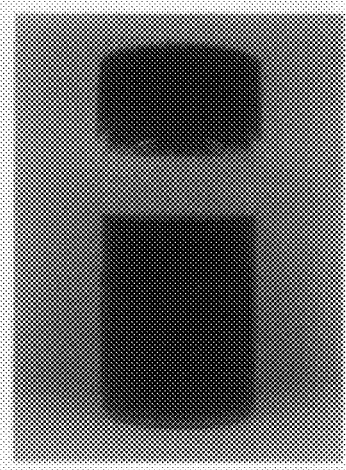

Preparation of Single-Walled Carbon Nanotube-Dispersed Liquid with Ionic Organic Compound The ionic organic compound 1•Cl (25 mg) was mixed with deionized pure water (5 ml) in a sample tube, followed by heating, to form a homogeneous solution. To the solution, single-walled carbon nanotubes (0.5 mg) prepared by a HiPco method (a high-pressure carbon monoxide method), were added. Ultrasound was applied to the mixture for 1 hour from an ultrasonic irradiation apparatus for cleaning (130 W, 35 kHz), to give a carbon nanotube-dispersed black solution, with no precipitate. The result is shown in FIG. 16, in which (a) is before the ultrasonic irradiation, and (b) is after the ultrasonic irradiation.

Figure 17:
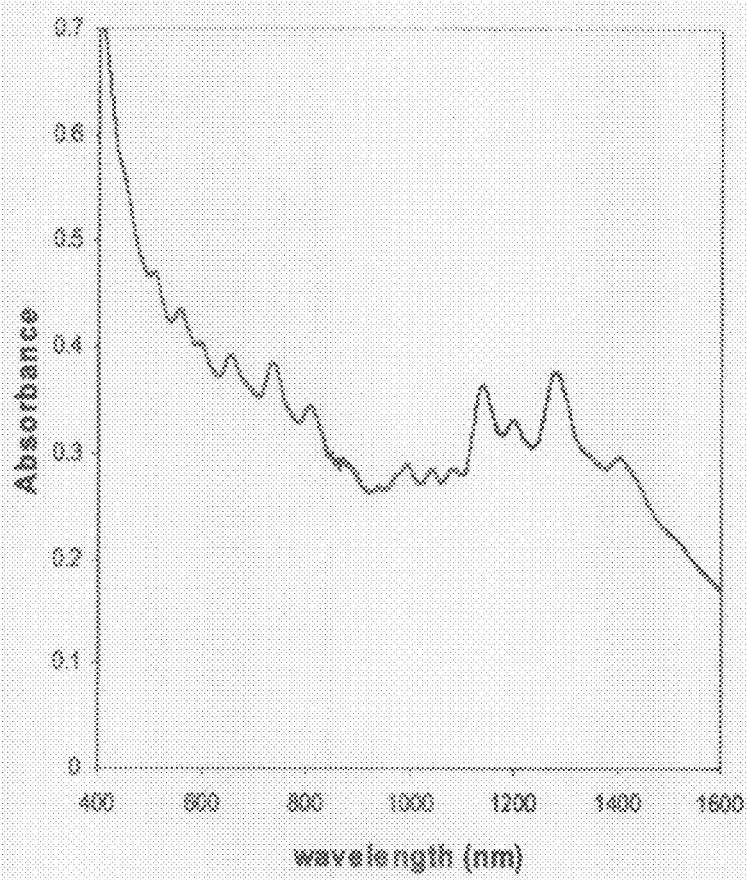
FIG. 17 is a near-infrared/UV spectrum of a single-walled carbon nanotube-dispersed aqueous liquid (solvent: heavy water) in Example 10 (horizontal axis: wavelength, vertical axis: absorbance).

The resultant solution did not show any precipitate, even when allowed to stand for at least half a year, and was observed to have a remarkable difference from the case where the ionic organic compound 1•Cl was not added. Further, the solubilization of the single-walled carbon nanotubes was also confirmed, based on the fact that a sawtooth absorption spectrum having continuous sharp absorptions characteristic of individually dispersed single-walled carbon nanotubes was clearly observed, in the wavelength range of 400 to 1,600 nm, when the dispersion liquid was prepared using heavy water as a solvent and measured for near infrared/UV spectrum. The result is shown in FIG. 17.

It is possible to appropriately determine, depending on the purpose, the blending ratio of each component in the dispersion liquid preparation; and it was confirmed that it is possible to easily prepare the carbon nanotube-dispersed liquid within the product 1 weight ratio range of 0.001 to 0.95% by weight and within the single-walled carbon nanotube weight ratio range of 0.001 to 0.3% by weight, respectively, to the solvent to be used.

Further, it was confirmed that it is possible to easily prepare the carbon nanotube-dispersed liquid when the anion X was Br or $BF_4$ in place of Cl. It was further confirmed that a carbon nanotube-dispersed liquid was also obtained by a similar method using the ionic organic compound 15•Cl in which the 'B' moiety of the basic skeleton was a urea group.

Example 11

Figure 18:
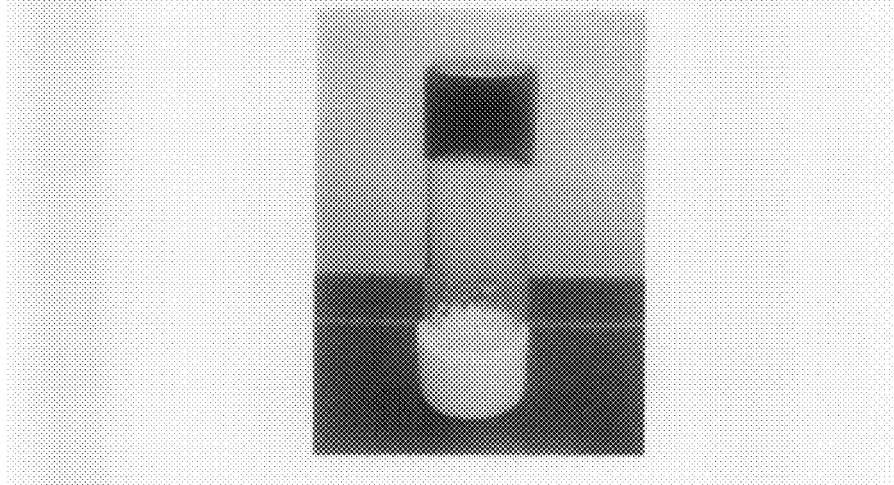
FIG. 18 is a photograph of a single-walled carbon nanotube-dispersed gel in Example 11 (in a vial turned upside down with a single-walled carbon nanotube content (concentration) of 0.02 mg/ml).

Preparation of Single-Walled Carbon Nanotube-Dispersed Gel with Ionic Organic Compound The dispersion liquid prepared in Example 10 was allowed to stand at room temperature in the opened sample tube, to make the solvent be gradually vaporized, thereby to give a single-walled carbon nanotube-dispersed black gel. FIG. 18 shows a photograph of the resultant gel.

It was also confirmed that direct synthesis of the gel was also possible by adding the ionic organic compound 1•Cl in a weight ratio of at least 1% by weight to the solvent. Specifically, the ionic organic compound 1•Cl (60 mg) was mixed with deionized water (5 ml) in a sample tube, and single-walled carbon nanotubes (0.1 mg) prepared by a HiPco method (a high-pressure carbon monoxide method) were further added thereto, followed by heating, to make the product 1 be dissolved. Ultrasound was then applied to the product 1 for 1 hour from an ultrasonic irradiation apparatus for cleaning (130 W, 35 kHz), and then the product was allowed to stand at room temperature, to give a similar carbon nanotube-dispersed gel. Concerning the production of the gel, when the falling of the liquid was not observed in the dispersion-containing sample tube turned upside down, it was judged that a gel state was occurred.

It is possible to appropriately determine, depending on the purpose, the blending ratio of each component in the gel preparation; and it was confirmed that it was possible to prepare easily the carbon nanotube-dispersed gel, within the ionic organic compound 1•Cl weight ratio range of 1 to 10% by weight, and within the single-walled carbon nanotube weight ratio range of 0.001 to 0.3% by weight to the solvent.

Example 12

Preparation of Single-Walled Carbon Nanotube-Dispersed Thin Film with Ionic Organic Compound The single-walled carbon nanotube-dispersed liquid (2 ml) prepared in Example 10 above, was spread on a quartz substrate, followed by drying in the air at room temperature for 12 hours, to give a carbon nanotube-containing thin film. While the spreading on the substrate was preformed by the casting method as described above, it was also confirmed that the preparation was possible by a spin coating method.

Figure 19:
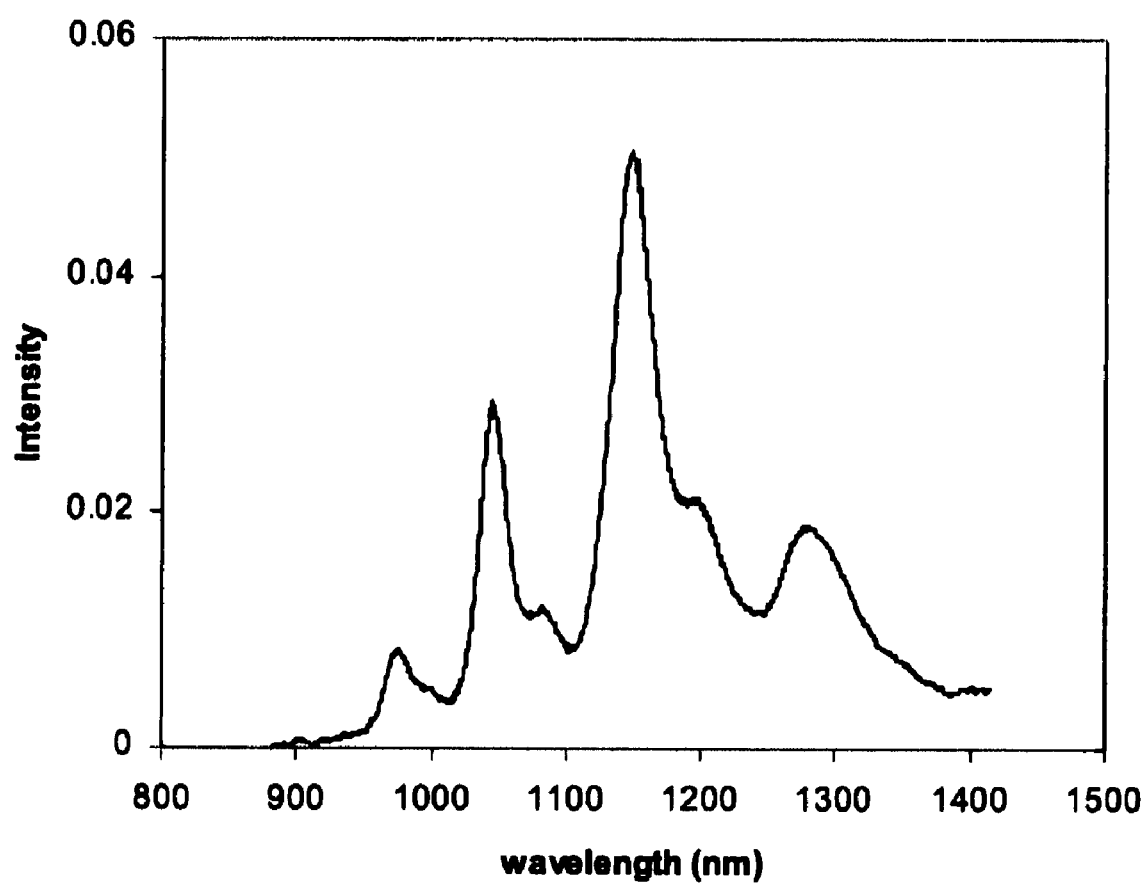
FIG. 19 is a fluorescence spectrum of a single-walled carbon nanotube-dispersed thin film (on a quartz substrate) in Example 12 (excitation wavelength: 662 nm, horizontal axis: wavelength, vertical axis: fluorescence intensity).

FIG. 19 is a fluorescence spectrum of the thus-prepared carbon nanotube-containing thin film. As shown in this figure, from the fluorescence spectrum of the thin film (excitation wavelength: 662 nm), characteristic luminescence peaks were observed within the wavelength range of 900 to 1,400 nm, which are only observed in the case of individually dispersed single-walled carbon nanotubes. Thus, it is found that the single-walled carbon nanotubes were individually dispersed at a molecular level even after the thin film was formed.

The invention claimed is:

1. An ionic organic compound, having a repeating unit represented by formula (I):

[Formula 1]

$$[-(A-B-C)_n-]\cdot m(X) \qquad (I)$$

wherein A represents a divalent quaternary ammonium cation-containing group derived from an aromatic heterocyclic compound containing at least one nitrogen atom, in which a left-ended bonding hand in formula (I) extends from the nitrogen atom of the quaternary ammonium cation, and in which a right-side bonding hand of A extends from a site other than said nitrogen atom in the aromatic heterocycle; B represents a functional group selected from an amide group, a urea group, a urethane group, and a peptide group, each of which may have a substituent; C represents an optionally substituted divalent aliphatic or aromatic hydrocarbon group linking A and B, in which B at the left side of C in formula (I) is linked, through said C, with A in the repeating unit -(A-B-C)$_n$- being next to the right side of said C; X represents an anion; n represents the number of repeating units; m represents the total number of anions; and n and m are the same integer and are each an integer of 2 to 30.

2. The ionic organic compound according to claim 1, wherein the aromatic heterocyclic compound is at least one selected from pyridine, pyrazine, pyrimidine, triazine, quinoline, isoquinoline, quinoxaline, imidazole, thiazole, and triazole, each of which may have a substituent.

3. The ionic organic compound according to claim 1 or 2, wherein X in formula (I) is at least one selected from a halogen atom (F, Cl, Br, or I), a tetrafluoroborate group (BF$_4$), a hexafluorophosphate group (PF$_6$), bis(trifluoromethanesulfonyl)imide, thiocyanate (SCN), a nitrate group (NO$_3$), a sulfate group (SO$_4$), a thiosulfate group (S$_2$O$_3$), a carbonate group (CO$_3$), a hydrogencarbonate group (HCO$_3$), a phosphate group, a phosphite group, a hypophosphite group, any halogen oxide acid group (XO$_4$, XO$_3$, XO$_2$, or XO, wherein X is Cl, Br or I), a tris(trifluoromethylsulfonyl)carbon acid group, a trifluoromethylsulfonate group, a dicyanamide group, an acetate group (CH$_3$COO), a haloacetate group ((CX$_n$H$_{3-n}$)COO, wherein X is F, Cl, Br, or I, and n is 1, 2 or 3), and a tetraphenylborate group (BPh$_4$) and a derivative thereof (B(Aryl)$_4$, wherein Aryl is a substituted phenyl group).

4. The ionic organic compound according to claim 1, wherein the compound is

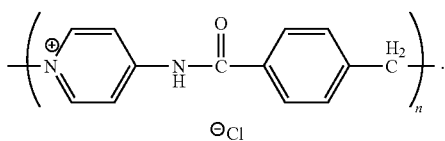

5. A method for producing the ionic organic compound according to claim 1, comprising allowing a heterocyclic compound containing at least one nitrogen atom having amino to undergo a condensation reaction with a halogenomethylcarboxylic acid halide having an active methylene group in its molecule or with an isocyanate compound having an active methylene group in its molecule.

6. The method according to claim 5, further comprising replacing the anion of the ionic organic compound with another anion by an anion exchange reaction.

7. A hydrogel-forming agent, comprising the ionic organic compound according to claim 1 as an essential component.

8. A hydrogel, comprising the hydrogel-forming agent according to claim 7.

9. The hydrogel according to claim 8, which has a high-speed storage modulus-recovery rate.

10. The hydrogel according to claim 9, wherein when the hydrogel with a concentration of 30 g/L is measured for dynamic viscoelasticity at 25° C., the resulting physical property values are: a storage modulus (G') of 1,000 Pa to 50,000 Pa and a loss tangent (tand) of at most 0.5 indicating quasi-solid properties, at a frequency of 6 rad/s and a distortion of 0.02%; and a storage modulus (Gs') of 1 Pa to 100 Pa and a loss tangent (tand) of at least 2 indicating quasi-liquid properties, at a frequency of 6 rad/s and a distortion of 100%, and when a distortion of 100% is continuously applied to the hydrogel for at least 1 minute, and immediately after that the resulting hydrogel be in a quasi-liquid state, the distortion is adjusted to 0.02% again, the hydrogel shows a storage modulus recovery rate (G'/G$_0$') of more than 75% within 10 seconds and shows a storage modulus recovery rate (G'/G$_0$') of more than 90% within 10 minutes, relative to its initial storage modulus value (G$_0$').

11. An ionic liquid-gelling agent, comprising the ionic organic compound according to claim 1 as an essential component.

12. An ionic liquid gel, comprising the ionic liquid-gelling agent according to claim 11.

13. The ionic liquid gel according to claim 12, which has at least 85% of an ionic conductivity before gelation.

14. A carbon nanotube-dispersing agent, comprising the ionic organic compound according to claim 1 as an essential component.

15. A carbon nanotube-dispersed liquid or gel, comprising the carbon nanotube-dispersing agent according to claim 14, carbon nanotubes, and a solvent comprising at least water.

16. A carbon nanotube-containing thin film produced from the carbon nanotube-dispersed liquid or carbon nanotube-dispersed gel according to claim 15.

17. The carbon nanotube-containing thin film according to claim 16, which is produced by spreading the carbon nanotube-dispersed liquid or carbon nanotube-dispersed gel on a substrate, followed by drying.

18. The carbon nanotube-containing thin film according to claim 16 or 17, wherein the carbon nanotubes are dispersed in such a manner that they are separated from one another.

19. A light-emitting material, comprising the carbon nanotube-containing thin film according to claim 16.

* * * * *